US009778020B2

(12) United States Patent
Tumlinson et al.

(10) Patent No.: US 9,778,020 B2
(45) Date of Patent: Oct. 3, 2017

(54) EFFICIENT INTERFEROMETER DESIGNS FOR OPTICAL COHERENCE TOMOGRAPHY

(71) Applicant: Carl Zeiss Meditec, Inc., Dublin, CA (US)

(72) Inventors: Alexandre R. Tumlinson, San Leandro, CA (US); Matthew J. Everett, Livermore, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 0 days.

(21) Appl. No.: 15/159,601

(22) Filed: May 19, 2016

(65) Prior Publication Data
US 2016/0341538 A1 Nov. 24, 2016

Related U.S. Application Data

(60) Provisional application No. 62/165,537, filed on May 22, 2015.

(51) Int. Cl.
*A61B 3/14* (2006.01)
*A61B 3/00* (2006.01)
(Continued)

(52) U.S. Cl.
CPC .......... *G01B 9/02015* (2013.01); *A61B 3/102* (2013.01); *G01B 9/02051* (2013.01); *G01B 9/02091* (2013.01); *G01B 2290/70* (2013.01)

(58) Field of Classification Search
USPC ................................................ 351/200–246
See application file for complete search history.

(56) References Cited

U.S. PATENT DOCUMENTS 5,459,570 A 10/1995 Swanson et al.
6,501,551 B1 12/2002 Tearney et al.
(Continued)

OTHER PUBLICATIONS

John et al., "Wideband Electrically Pumped 1050-nm MEMS-Tunable VCSEL for Ophthalmic Imaging", Journal of Lightwave Technology, vol. 33, No. 16, Aug. 15, 2015, pp. 3461-3468.
(Continued)

*Primary Examiner* — Mohammed Hasan
(74) *Attorney, Agent, or Firm* — Morrison & Foerster LLP

(57) ABSTRACT

Efficient interferometer designs for optical coherence tomography (OCT) systems are presented. One example interferometer design includes two polarization dependent beamsplitters and a non-polarization dependent combiner. The first polarization dependent beamsplitter transmits light in a first polarization state to a sample arm of the OCT system and transmits light in a second polarization state different from the first polarization state to a reference arm of the system. The second polarization dependent beamsplitter transmits light returning from a sample to the non-polarization dependent combiner. The combiner combines light returned from the sample and the light that has passed through the reference arm, which is then detected at a detector. Another example interferometer design includes free space optics comprising a non-reciprocal beamsplitting element in a beam path from a light source to a sample. The non-reciprocal beamsplitting element is implemented using a combination of a polarization dependent beamsplitter and a polarization manipulator.

20 Claims, 17 Drawing Sheets

(51) Int. Cl.
    *G01B 9/02*   (2006.01)
    *A61B 3/10*   (2006.01)

(56) References Cited

U.S. PATENT DOCUMENTS

| | | |
|---|---|---|
| 6,657,727 B1 | 12/2003 | Izatt et al. |
| 7,102,756 B2 | 9/2006 | Izatt et al. |
| 7,126,693 B2 | 10/2006 | Everett et al. |
| 7,145,661 B2 | 12/2006 | Hitzenberger |
| 7,280,221 B2 | 10/2007 | Wei |
| 7,388,672 B2 | 6/2008 | Zhou et al. |
| 7,400,410 B2 * | 7/2008 | Baker ............... A61B 3/1005 351/210 |
| 2013/0208240 A1 * | 8/2013 | Sharma ............... A61B 3/102 351/206 |

OTHER PUBLICATIONS

Yun et al., "Pulsed-Source and Swept-Source Spectral-Domain Optical Coherence Tomography with Reduced Motion Artifacts", Optics Express, vol. 12, No. 23, Nov. 15, 2004, pp. 5614-5624.

* cited by examiner

EFFICIENT INTERFEROMETER DESIGNS FOR OPTICAL COHERENCE TOMOGRAPHY

PRIORITY

The present application claims priority to U.S. Provisional Application Ser. No. 62/165,537 filed May 22, 2015, the contents of which are hereby incorporated by reference.

BACKGROUND

Optical Coherence Tomography (OCT) is an interferometric technique for performing high-resolution cross-sectional imaging that can provide images of samples including tissue structure on the micron scale in situ and in real time. OCT is based on the principle of low coherence interferometry (LCI) and determines the scattering profile of a sample along the OCT beam by detecting the interference of light reflected or scattered from a sample and a reference beam. Each scattering profile in the depth direction (z) is called an axial scan, or A-scan. Cross-sectional images (B-scans), and by extension 3D volumes, are built up from many A-scans, with the OCT beam moved to a set of transverse (x and y) locations on the sample. In time domain OCT (TD-OCT), the path length between light returning from the sample and reference light is translated longitudinally in time to recover the depth information in the sample. In frequency-domain or Fourier-domain OCT (FD-OCT), a method based on diffraction tomography, the broadband interference between reflected sample light and reference light is acquired in the spectral frequency domain and a Fourier transform is used to recover the depth information. The sensitivity advantage of FD-OCT over TD-OCT is well established.

There are two common approaches to FD-OCT. One is spectral domain OCT (SD-OCT) where the interfering light is spectrally dispersed prior to detection and the full depth information can be recovered from a single exposure. The second is swept-source OCT (SS-OCT) where the source is swept over a range of optical frequencies and detected in time, therefore encoding the spectral information in time. In traditional point scanning or flying spot techniques, a single point of light is scanned across the sample. The techniques have found great use in the field of ophthalmology.

Optical coherence tomography is able to observe extremely weak reflections in a sample and locate those reflections with high accuracy. When an OCT system is functioning optimally it is described as functioning close to the shot noise limit, indicating that signal-to-noise ratio is absolutely limited by the number of photons exiting the sample and being collected by its detectors. The power with which a sample such as the eye can be illuminated is limited potentially by safety and by the availability of source power available at a particular cost. Therefore, it has been a goal of OCT designers since the beginning of the field to develop interferometers and optical components which optimize the efficiency of light transfer, most critically in the direction from the sample to detector, but also with regard to the total amount of light produced by the source.

In order to achieve shot noise limited detection, the amount of power in the reference arm must be optimized. If the power in the reference is too low, detector noise dominates. If the power in the reference arm is too high, relative intensity noise from the source may dominate. Mechanical and optical tolerances and design uncertainty are frequently larger than the optimum reference arm power window, therefore adjustable elements are frequently built into OCT systems to allow compensation. A stable, low cost, and high efficiency means to adjustably set the reference arm power is desirable. A number of efficient interferometer designs have been proposed in the prior art (see for example, U.S. Pat. Nos. 7,388,672, 7,126,693, 7,145,661, 7,102,756, 6,657,727, 7,280,221, 6,501,551, 549,570, all of which are hereby incorporated by reference).

Some of the limitations that are associated with the prior-art interferometer designs are 1) lossy fiber coupling at the source which limits the utility of low power sources; 2) non-reciprocal beamsplitting ratios are implemented using faraday circulators, which are currently not available at low cost at ophthalmic wavelengths of 840 and 1050 nm; 3) incompatibility with dual balanced detection, typically required for swept source OCT; 4) fixed power ratios in the sample and reference arm, or lossy attenuating elements are required in the reference arm to set optimal power; and 5) need of polarization elements/optics in the reference and/or detection arms to select from input polarization states the components of the sample and reference which have the same polarization states.

Here, we propose some improved interferometer designs over the prior-art designs for use with OCT systems. The improved designs are cost effective (by involving minimal or low cost optics), improve the overall optical efficiency of light transmission for maximum signal detection, and are highly compatible with dual balanced detection.

SUMMARY

According to one aspect of the subject matter described in the present application, an interferometer for use in an optical coherence tomography (OCT) imaging system having a source arm with an optical radiation source, a sample arm, a reference arm, and a detector includes a first polarization dependent splitting element having an input port connected to the optical radiation source, a first output port connected to the sample arm leading to a sample, said first output port transmitting light in a first polarization state towards the sample, and a second output port connected to the reference arm, said second output port transmitting light in a second polarization state different from the first polarization state; a second polarization dependent splitting element having an input port connected to the sample arm and an output port; and a substantially non-polarization dependent combiner having a first input port for receiving light that has passed through the sample arm from the output port of the second polarization dependent splitting element, a second input port for receiving light from the reference arm, and an output port connected to the detector.

The interferometer design according to the above aspect is particularly advantageous in a number of respects. By way of example and not limitation, (1) the design uses only components which are available at low cost at the dominant ophthalmic wavelengths of 840 and 1050 nm, (2) it is highly compatible with dual balanced detection, (3) polarizing optics are used to achieve a flexible splitting ratio of source light between the sample and reference arms, (4) when light returning from the sample is combined with reference light at a non-polarizing dependent combiner or beamsplitter, the beams are in the same polarization state and can interfere with high efficiency without a polarization diverse detection, and (5) the design eliminates the need for polarization rotating optics in the reference arm and a polarization element in the detection path which was previously required to select from the input polarization states the components of the sample and reference which had the same polarization state. In doing so, the design improves the optical efficiency, reduces cost, and enables dual balanced detection.

According to another aspect of the subject matter described in the present application, an interferometer for use in an optical coherence tomography (OCT) imaging system having a swept light source, a sample arm leading to a sample to be imaged, a reference arm, and a dual balanced detector includes free space optics for directing light from the swept light source to the sample, said free space optics comprising non-reciprocal beamsplitting elements including a polarization dependent beamsplitting element and a polarization manipulator, said polarization dependent beamsplitting element having an input port for receiving light from the swept light source, a first output port for sending light towards the sample, and a second output port for transmitting light returning from the sample, said polarization manipulator configured to manipulate the polarization state of the light transmitted through the manipulator and is located in between the polarization dependent beamsplitting element and the sample; and a non-polarization dependent combiner having a first input port for receiving light returning from the sample from the polarization dependent beamsplitting element, a second input port for receiving light from the reference arm, and an output port connected to the dual balanced detector.

The interferometer design according to this aspect is particularly advantageous in a number of other respects. By way of example and not limitation, the design involves an efficient combination of free space optics from the light source to a sample (e.g., human eye) with a non-reciprocal beamsplitting element and dual balanced detection. By allowing a hybrid interferometer design with only free space optics in the path from the source to the sample, but allowing single mode fiber in the reference path and in path returning from the sample, the design maintains many of the advantages of a fiber implementation while maximizing the utilization of valuable source power.

According to yet another aspect of the subject matter described in the present application, an interferometer for use in an optical coherence tomography (OCT) imaging system having an optical radiation source, a sample arm, a reference arm, and a detector includes a polarization dependent splitting element having a first port for receiving light from the optical radiation source, a second port for transmitting light in a first polarization state to the sample arm, a third port for transmitting light in a second polarization state different from the first polarization state to the reference arm, and a fourth port for transmitting light returned from the sample arm; and a substantially non-polarization dependent combiner having a first input port for receiving light that has passed through the sample arm and exited through the fourth port of the polarization dependent splitting element, said non-polarization dependent combiner having a second input port for receiving light from the reference arm, said non-polarization dependent combiner having an output port connected to the detector.

The interferometer design according to this aspect is particularly advantageous in a number of other respects. By way of example and not limitation, the polarization dependent beamsplitting element is used as a four port device instead of a three port device. This four port configuration provides the advantage of flexible control of the beamsplitting ratio to the reference arm and simplifies the optical path.

It should be noted that the above aspects of interferometer designs are not entirely independent and can be combined with one another to be used with OCT systems.

The features and advantages described herein are not all-inclusive and many additional features and advantages will be apparent to one of ordinary skill in the art in view of the figures and description. Moreover, it should be noted that the language used in the specification has been principally selected for readability and instructional purposes and not to limit the scope of the inventive subject matter.

BRIEF DESCRIPTION OF THE DRAWINGS

FIG. 3b illustrates further details of the beam path shown and discussed in the embodiment of FIG. 3a.

DETAILED DESCRIPTION

Figure 1:
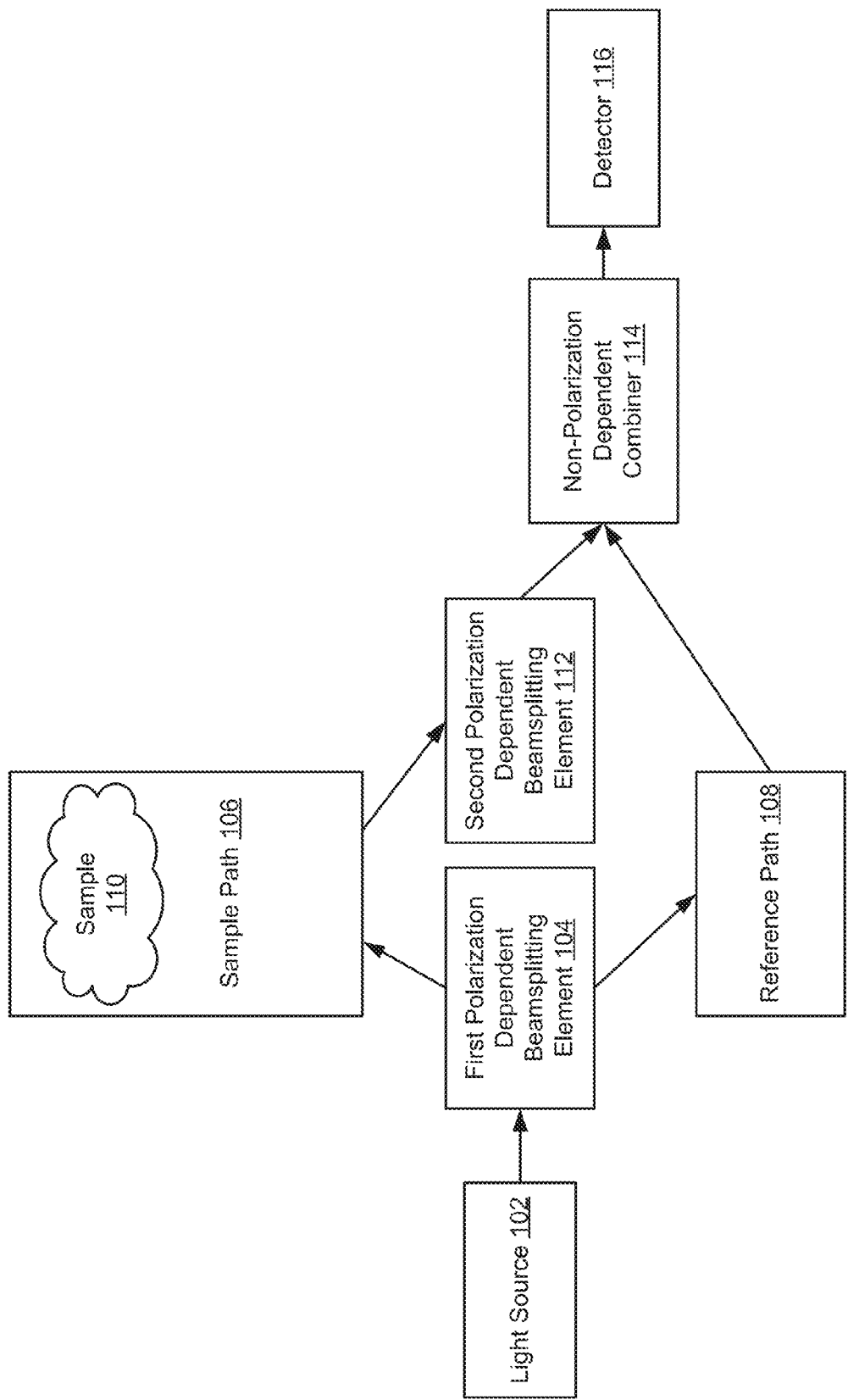
FIG. 1 is a block diagram illustration of one aspect of the present invention.

FIG. 1 is a block diagram illustration of one aspect of the present invention. It should be understood that this illustration is just a general or a high level overview of this aspect of the invention and more specific details with respect to different interferometer designs will be discussed later below, for example, with respect to at least FIGS. 3A, 3B, 4-14.

In some instances, some of the steps in this block representation, although not shown, may be performed by specific optical components such as coatings, fiber, waveplates, blocks of glass, lenses, scanners, eyes, endoscopes etc. Additionally, multiple steps may be performed by a single optical coating in one implementation, where they are performed by two distinct surfaces or components in another.

Referring to FIG. 1, light from a source 102 is directed towards a first polarization dependent beamsplitting element 104 which divides the light into two component polarizations. These two component polarizations may be orthogonal to one another. One of these components is delivered to a sample path 106 and a second is delivered to a reference path 108. In the sample path 106, the light is incident on a sample 110 which will scatter and/or reflect some light towards a second polarization dependent beamsplitting element 112. The second polarization dependent beamsplitting element 112 will separate the input light into two component polarizations. One of the component polarizations will be directed towards a non-polarization dependent combiner 114. In some embodiments, the component polarization that is transmitted to the combiner 114 is the same as the component polarization that was transmitted or delivered to the reference path 108, as discussed in further detail below. Light from the reference path 108 is also directed towards the non-polarization dependent combiner 114. Combined light from the non-polarization dependent combiner 114 is measured by a detector 116. In some embodiments, the first polarization dependent beamsplitting element 104 and the second polarization dependent beamsplitting element 112 may be the same and are combined into one single beamsplitting element (see for example, polarization beamsplitter 303 in FIGS. 3A and/or 3B or the polarization dependent beamsplitting element 1600 in FIG. 16). In other embodiments, the two beamsplitting elements 104 and 112 may be separate elements or entities as shown and discussed, for example, with respect to FIG. 14. It should be understood that this aspect of the present invention discussed herein is not limited to the elements shown in FIG. 1 and that additional beamsplitting, combining, and detection elements may be inserted along the light paths. Additional alterations which convert one polarization state to another polarization state may also be introduced along the beam paths. Additional beam shaping, scanning, or modulation elements may also be added along the basic beam paths illustrated, as discussed in further detail below.

Figure 16:
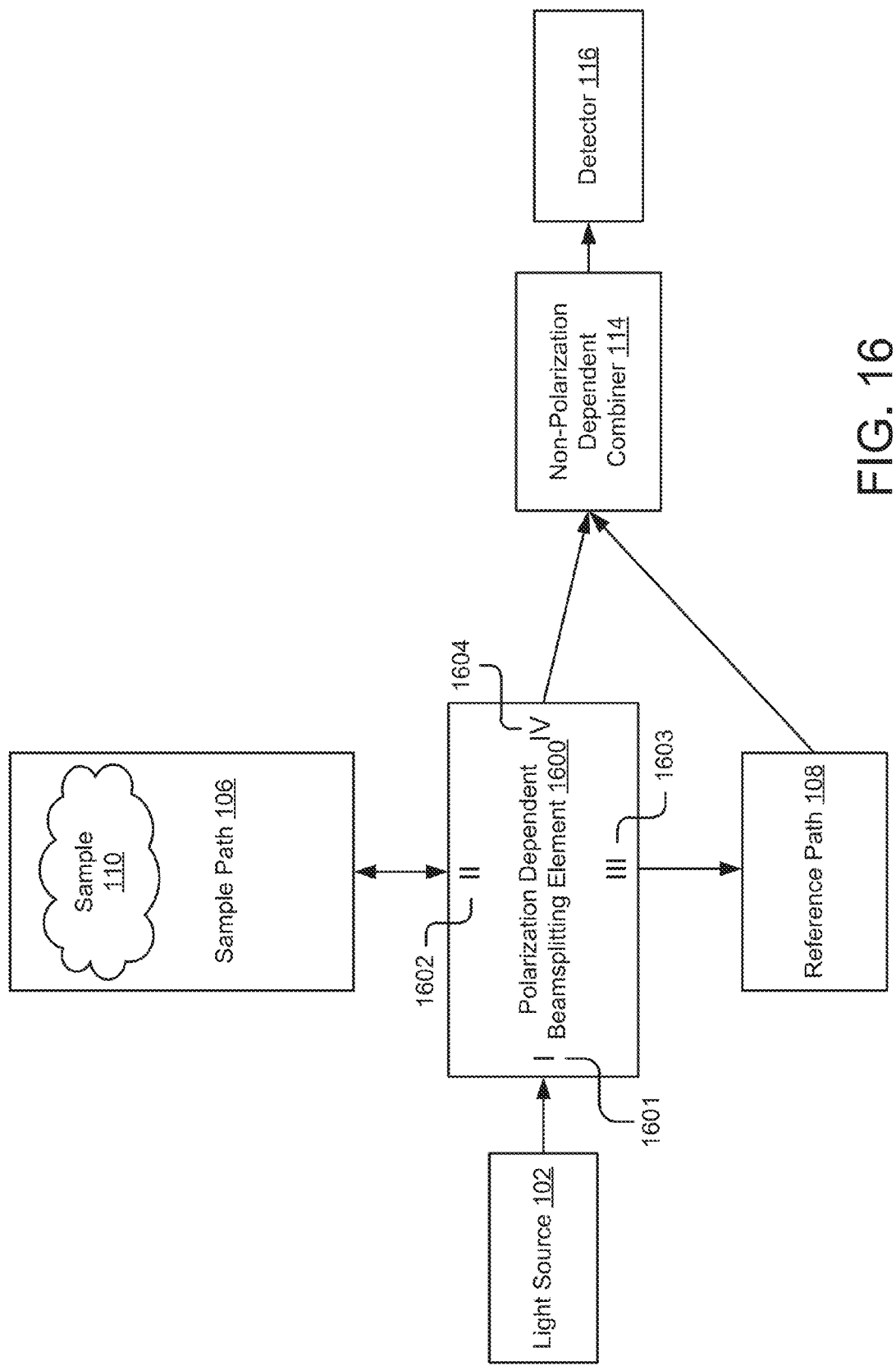
FIG. 16 is a block diagram illustration of another aspect of the present invention.

FIG. 16 is a block diagram illustration of another aspect of the invention. This aspect is similar to the aspect depicted in FIG. 1 except that the first polarization dependent beamsplitting element 104 and the second polarization dependent beamsplitting element 112 are combined into one single polarization dependent beamsplitting element 1600, which is used as a four-port device. For instance, as depicted, 1) a first port or input port 1601 is used to receive light from the light source 102, 2) a second port is used to transmit light in a first polarization state to the sample path 106, 3) a third port is used to transmit light in a second polarization state orthogonal to the first polarization state to the reference path 108, and 4) a fourth port is used to transmit light returning from the sample 110 to the non-polarization dependent combiner 114.

Figure 2:
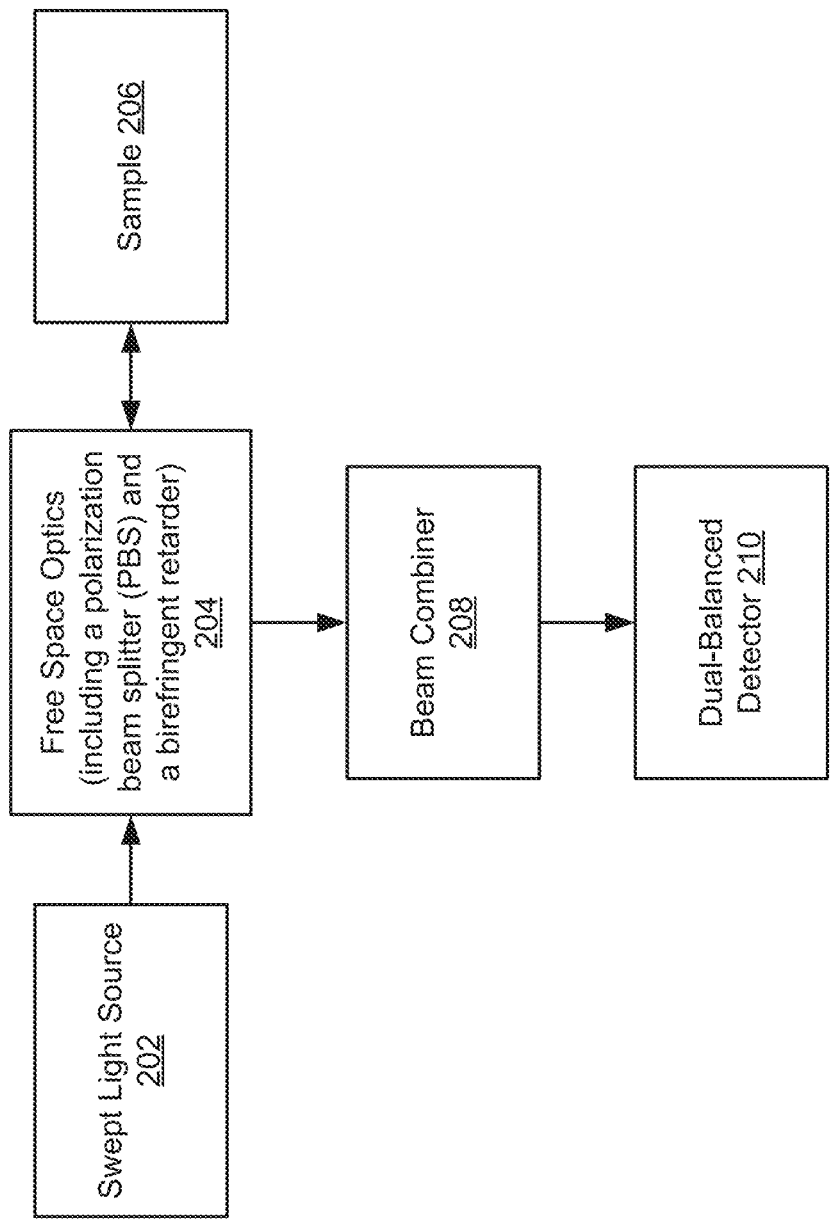
FIG. 2 is a block diagram illustration of another aspect of the present invention.

FIG. 2 is a block diagram illustration of another aspect of the present invention. Again, it should be understood that this illustration is just a general or a high level overview of this aspect of the invention and more specific details with respect to different interferometer designs will be discussed later below, for example, with respect to at-least FIGS. 3A, 3B, 4-7, 9, and 15. This aspect relates to OCT imaging of a sample (e.g., anterior or posterior regions in a human eye) 206 using a light source 202 as illustrated generally in FIG. 2. In some embodiments, the light source 202 is a swept source with an output optical power of less than 5 mW. One of the critical issues/concerns in the prior interferometer designs is high optical efficiency from the semiconductor optical light source to the sample (e.g., eye), and back to a detection. Fiber coupling at the semiconductor source is a major source of inefficiency, even for semiconductor sources producing a high quality single mode output. Therefore, in this aspect of the invention, firstly all beam paths between the semiconductor light source 202 and the sample 206 are conducted in bulk or free-space optics 204, without a restriction to single mode optical fiber. The free-space optics include a non-reciprocal ratio beamsplitting, which is implemented using a polarization beam splitter (PBS) and a birefringent material (e.g., quarter wave plate) to rotate the polarization in the sample arm at ophthalmically relevant wavelengths around 800 nm or 1050 nm. Such a non-reciprocal ratio beamsplitting arrangement causes the majority of light from the source 202 to be directed towards the sample 206, and a majority of light returning from the sample 206 to be directed towards a detector, such as a dual-balanced detector 210. Optics handling the light returned from the sample 206 include at-least a beam combiner 208 (e.g., a non-polarization dependent combiner) for combining the returning sample light with a reference light and may, in contrast to the path towards the sample 206, contain a restriction to single mode fiber although this is not required to practice this aspect of the invention. Finally, after the two beams are combined by the beam combiner 208, the combined beam is detected by a dual balanced detector 210 where two detectors measure interference 180 degrees out of phase with a processing such that fluctuations in intensity common to both detections can be canceled. This enables cancellation of fluctuations in the source power for instance. The arrangement as illustrated and discussed with reference to FIG. 2 provides advantages with respect to optical efficiency, signal purity, and cost relative to the prior art as will be clear from specific embodiments (e.g., FIGS. 3A, 3B, 15, etc.) illustrated below. Elements from the specific embodiments may be combined in multiple ways, or additional modifications made while still in the spirit of the invention illustrated in FIG. 2.

Figure 14:
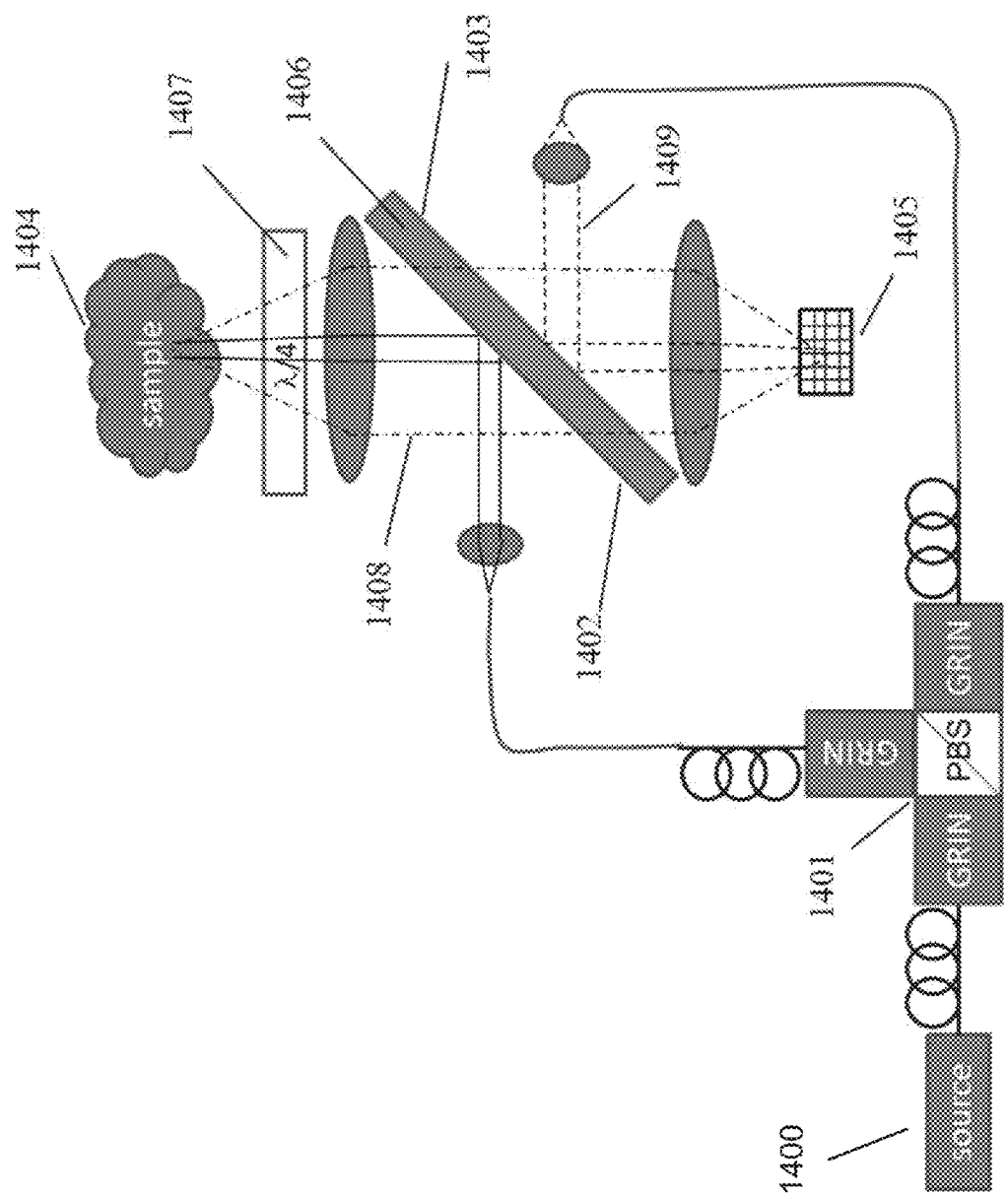
FIG. 14 is a schematic illustration of another exemplary interferometer design according to the present invention.
Figure 15:
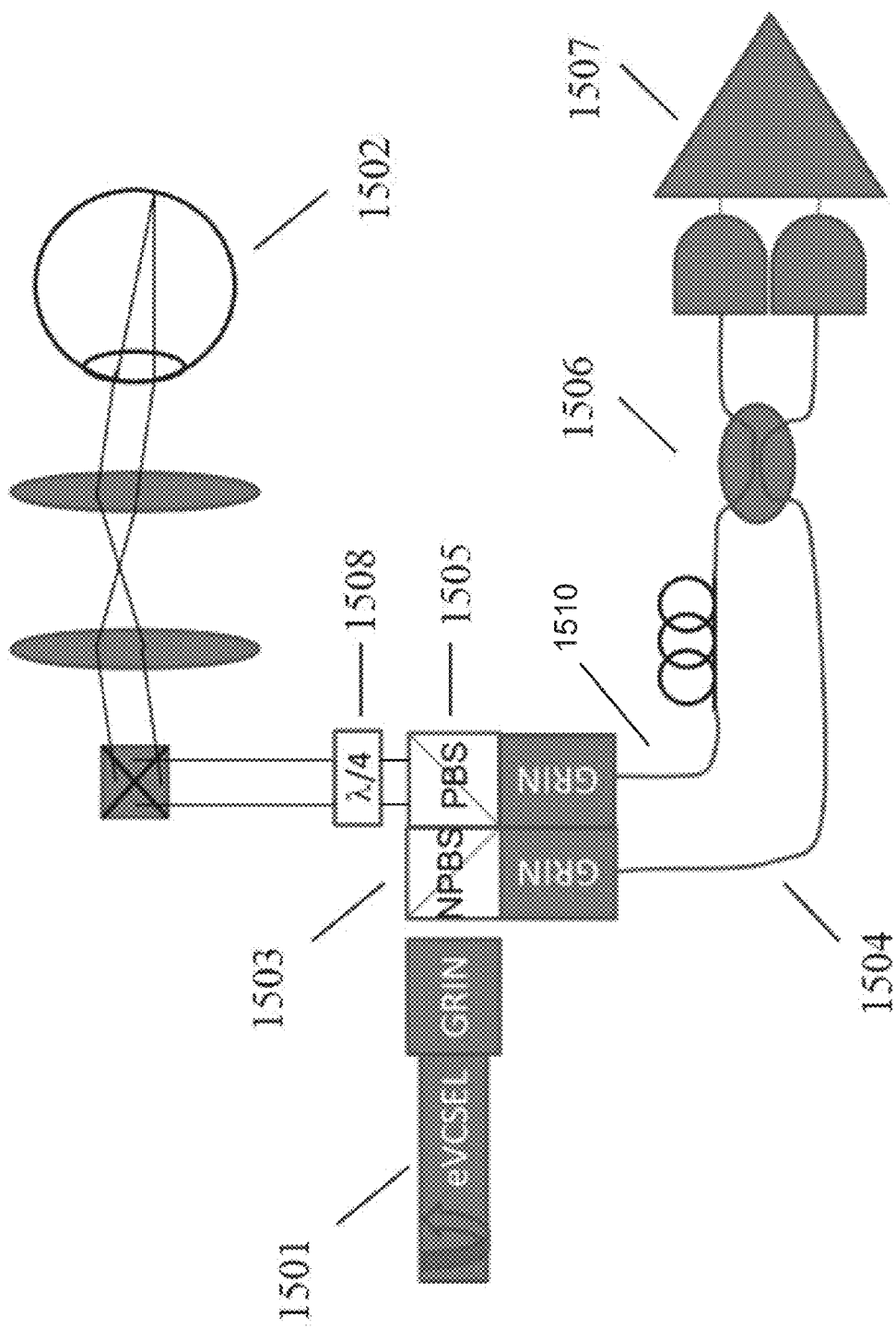
FIG. 15 is a schematic illustration of another exemplary interferometer design according to the present invention.

Different interferometer designs/embodiments are now described with respect to FIGS. 3A, 3B, and 4-15. The interferometer described in each of these embodiments is based on one or more of the aspects discussed above with respect to FIGS. 1, 2 and 16. For instance, the interferometer embodiments illustrated in FIGS. 3A, 3B, 4-7, and 9 are based on a combination of the aspects discussed in reference to FIGS. 1, 2, and 16. The embodiments illustrated in FIGS. 8, 10-13 are based on a combination of the aspects discussed in reference to FIGS. 1 and 16. The embodiment illustrated in FIG. 14 is based on the aspect discussed in FIG. 1 and the embodiment illustrated in FIG. 15 is based on the aspect discussed in FIG. 2. It should be understood that the present disclosure is not limited to these embodiments and a variety of other embodiments based on one or more of the aspects of FIGS. 1, 2, and/or 16 may be employed and are within the scope of the present disclosure.

Figure 3A:
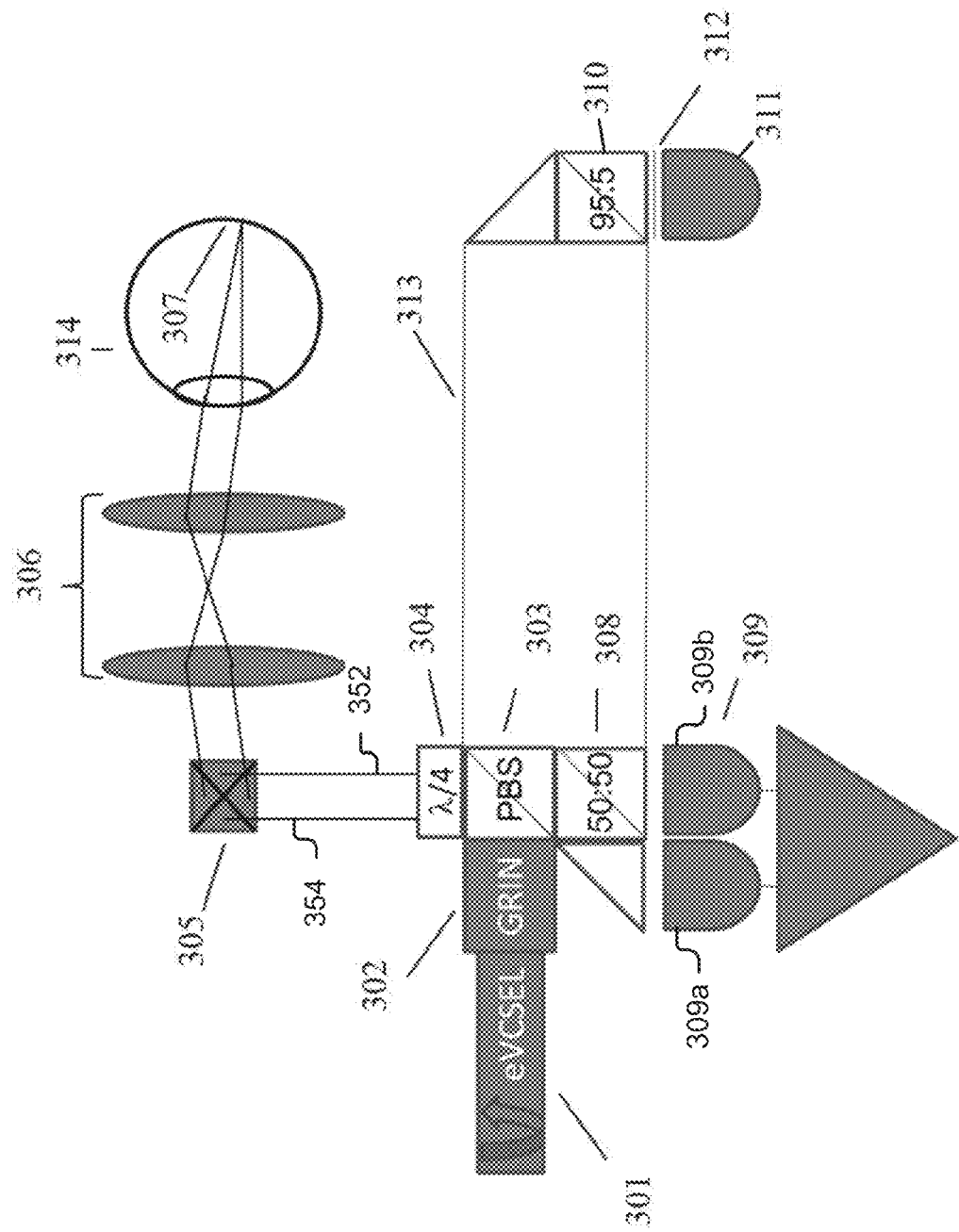
FIG. 3a is a schematic illustration of one exemplary interferometer design/embodiment according to the present invention.

FIG. 3a is a schematic illustration of one exemplary interferometer design. In some instances, the embodiment illustrated in FIG. 3a is based on a combination of the aspects discussed with respect to FIGS. 1, 2, and 16. It should be noted that new reference numerals are used to refer to the elements/entities associated with this embodiment. However, one should not be confused or interpret that these elements are entirely different from the elements discussed with respect to FIGS. 1, 2, and/or 16. Specific descriptions have been added whenever an element relates to or corresponds with an element in FIG. 1, 2, and/or 16.

The interferometer discussed in FIG. 3A is optimized for a point scanning, swept source measurement with a low power source, and dual balanced detection. Here, the source 301 is illustrated as an electrically pumped tunable vertical cavity surface emitting laser (eVCSEL) with a fixed polarization state relative to its mechanical housing. A prototype laser with similar characteristics has been demonstrated by Praevium at 1050 nm with a bandwidth approximately 64 nm and a power of approximately 367 uW without subsequent amplification (see for example, John, D., et al. (2015). "Wideband Electrically-Pumped 1050 nm MEMS-Tunable VCSEL for Ophthalmic Imaging." Journal of Lightwave Technology: 1-1). While electrically pumped tunable VCSEL powers will almost certainly rise compared to their early prototype status, the very small gain volume of the devices precludes them from supporting the current levels and output powers commonly seen with edge emitting semiconductor lasers and optical amplifiers. To achieve optical powers usable for most OCT applications, similar VCSEL lasers have been used as a seed source, and subsequently mated to a semiconductor amplifier to produce approximately 20 mW output power desired for state of the art lossy interferometer designs.

As depicted in FIG. 3A, a gradient index lens (GRIN) 302 is used to approximately collimate the light before it is split into component polarization states by a multilayer dielectric coating in a polarization beam splitter cube (PBS) 303. It should be noted that although a single PBS 303 is shown in this FIG. 3A or in later figures of the present disclosure, the PBS 303 is capable of performing two beamsplittings as discussed with reference to the first polarization dependent beamsplitting element 104 and the second polarization beamsplitting element 112 in FIG. 1. That is, the PBS 303 may perform the function of the first polarization beamsplitting element 104 as the light travels in the direction towards the sample 307 and the same PBS 303 may perform the function of the second polarization beamsplitting element 112 when the light transmits through it on the return path from away from the sample 307. Also, it should be noted that the PBS 303 is used here as a four port device similar to the polarization dependent beamsplitting element 1600 discussed in FIG. 16.

The dielectric coating in the PBS 303 reflects light in a linear polarized 'S' state (in-out of the page i.e., one which has an electric field perpendicular to a plane of incidence), and transmits light in an orthogonal, linear polarized 'P' state (in the plane of the page i.e., one which is parallel to the plane of incidence). The fraction of light transmitted to each state is dependent on the alignment of the input polarization state and the decomposition into the component output states. Assuming a linear input state, the fraction of light power in each state is ideally $\cos^2(\theta)$, where theta is the angle between the input linear state and the orientation of each component state respectively. The mounting of the laser 301 may be rotated relative to the PBS 303 to set the reference arm power, after which it may be fixed in place. 'S' polarized light when incident on the PBS 303 is reflected into the sample arm (indicated by signal line 352, see FIG. 3B) and passes through a polarization manipulating element (e.g., a birefringent quarter wave plate) 304 with its fast axis oriented at 45 degrees relative to the incident polarization state. The quarter wave plate 304 is shown cemented directly to the PBS 303. In some instances, the waveplate 304 may be separated from the PBS 303, as shown for example in FIG. 5. Light transmitting through the quarter wave plate 304 acquires an approximately circular polarization. Circularly polarized light is transmitted through a scanner 305 for moving the beam to different lateral locations on the sample, next optics 306 to shape and focus the beam, through the anterior portion of the human eye 314 and ultimately to the object of interest, in this case, the sensory retina 307. The length of the sample arm 352 can be adjusted by changing the length of the space between the PBS 303 and the scanner 305. It should be noted that specific beam paths including sample path (i.e., light transmitting from the PBS 303 to the sample arm leading to the eye 314), detection path (light returning from the eye 314 back to the PBS 303), and the reference path (i.e., light transmitting from the PBS 303 to the reference arm) are shown and further discussed with respect to FIG. 3B.

When light is reflected or scattered back (indicated by signal line 354, see FIG. 3B) in a single scattering event, it retains its polarization, although its polarization may be altered as the light passes through birefringent material such as the cornea or retinal nerve fiber layer. In general, the retardance of these layers is a small fraction of a wavelength and changes the polarization state by a small amount, making the polarization state slightly elliptical. Light passes back along the same beam path through the optics of the eye, focusing optics 306, and is de-scanned by the scanner 305 such that it is again a static beam traversing the quarter waveplate 304, which introduces a quarter wave of retardance. Because the total retardance in the sample arm acts approximately as a half waveplate, oriented at 45 degrees to the input linear polarization, the output polarization is rotated approximately twice that angle to produce light that is primarily polarized in the orthogonal linear polarization (i.e., the 'S' polarized light that was initially transmitted to the sample arm 352 is now in 'P' polarized state). The light is then split again at the PBS 303 such that the dominant 'P' state is transmitted through the polarizing beamsplitter cube 303, and any 'S' component is reflected back in the direction of the source 301. In the ideal case, all the light backscattered from the sample would be 'P' polarized and therefore would all be transmitted through the PBS 303 on its way to the detector, such as the detector 309.

An equal ratio non-polarization dependent beamsplitter cube (NPBS) 308 (also referred to as the non-polarization dependent combiner 114 in FIG. 1) is cemented to the PBS 303. A monolithic glass path 313 cemented to both the PBS 303 and the NPBS 308 transmits the reference light from the PBS 303 to the NPBS 308. This monolithic path 313 is composed of multiple cemented prisms and glass block elements. A glass spacer block (i.e., block embedded within the monolithic glass path 313) provides a beam path through which the reference beam passes, but does not reflect or significantly refract the beam. The polarization state 'P' of the reference light (e.g., see reference light 353 in FIG. 3B) that was transmitted on the first splitting by the PBS 303 is maintained as it reflects off simple flat surfaces. The 'P' polarization state transmitted from the sample path through the PBS 303 on the second splitting is parallel to the 'P' polarization transmitted through the same dielectric surface to the reference arm in the first splitting. The NPBS 308 divides each incident light beam (sample 352, return 354, and reference 353 (see FIG. 3B)) into two equal parts directed to the detectors 309a and 309b, respectively, of a dual balanced detector 309. The spatial alignment of the beams is such that the sample return 354 and reference 353 have a large degree of spatial overlap at the detectors. When these parallel polarization states combine on a detector, they interfere with high contrast. The interference detected on the two detectors 309a and 309b of the dual balanced detector 309 is 180 degrees out of phase. Each detector shown may be a single element detector or may be an array detector in one or two dimensions.

In the case of array sampling, it may be advantageous to introduce a small tilt between the sample and reference light to introduce an 'off-axis reference.' In the case that the reference is 'on-axis', the sample return and the reference have a high degree of spatial overlap at the detector 309 and at the NPBS 308. Phase variation over the surface of the detector is minimized. In the case of 'off-axis' reference, spatial overlap of the two beams (i.e., returning beam 354 and the reference beam 353 (see FIG. 3B)) is maximized at the detector, and the beams may be slightly displaced from each other at the NPBS 308. A deliberate phase ramp is introduced over the surface of the detector which must be adequately sampled by the array. One reflecting corner of the monolithic reference arm path 313 is shown as partially transmissive using a 95:5 beamsplitter 310 to allow a small amount of light pass to an auxiliary detector 311 (see for example in FIG. 3B) which serves to monitor the power emitted by the laser and the instantaneous optical frequency. A small etalon 312 in the monitor path provides an interference reference for the optical frequency.

Figure 3B:
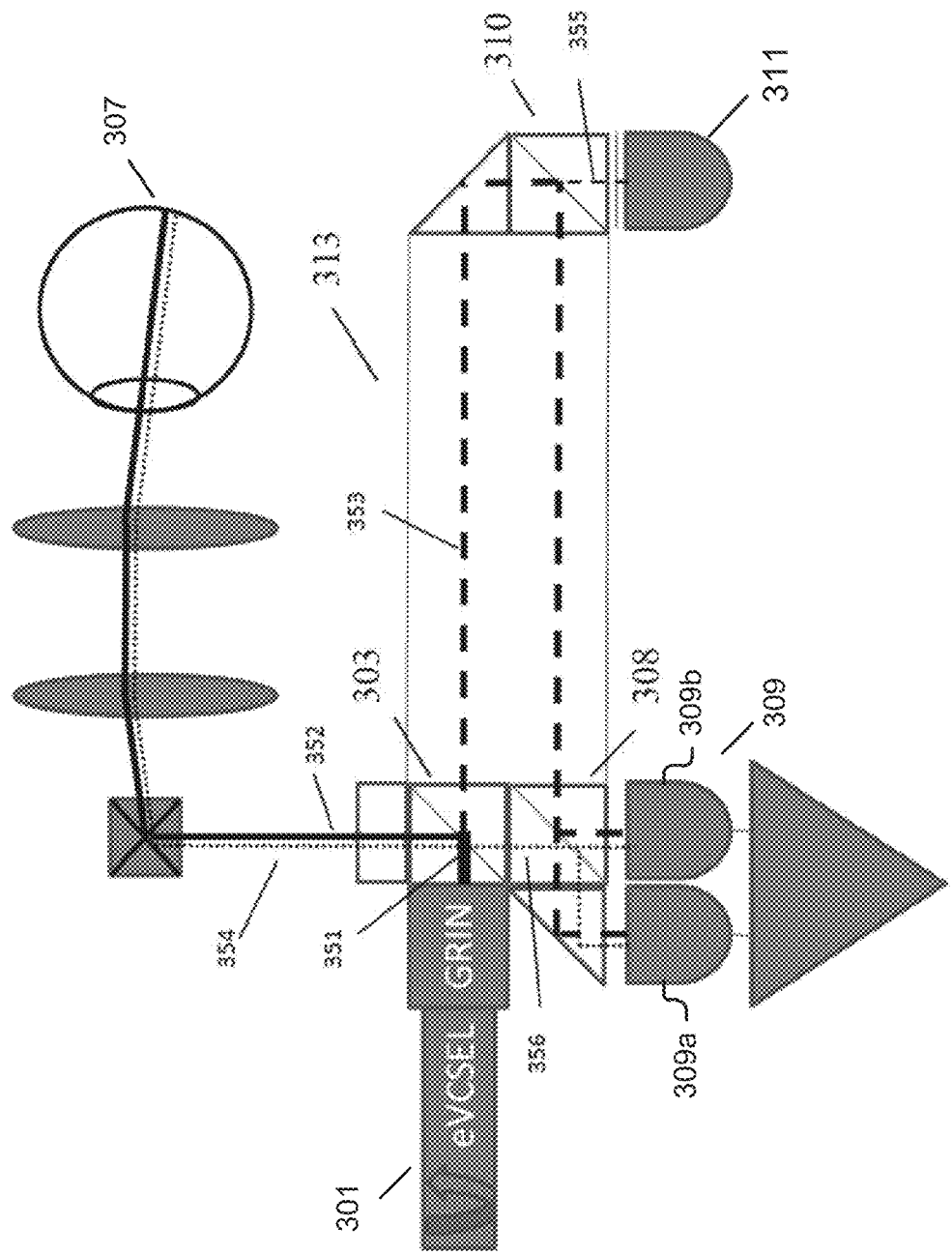

FIG. 3B illustrates further details of the beam paths shown and discussed in the embodiment of FIG. 3A. As depicted, same reference numerals are used to refer to the elements that have already been discussed above with respect to FIG. 3A. After the GRIN 302, light from the source 301 (indicated by signal line 351) is split at the PBS 303 into light which illuminates the sample (as shown by solid line 352) and reference light (as shown by dashed line 353). Sample return light (as shown by dotted line 354), which has been reflected or scattered from the sample 307 is transmitted with high efficiency in a second pass through the PBS 303 (as shown by dotted line 356). The sample return light (356) is then split into two equal portions by the NPBS 308. Reference light (353) takes a path through the monolithic block 313 of cemented optics including spacers and prisms until it also is split into two equal portions at the NPBS 308. At each detector element (309*a* or 309*b*) of the balanced detector 309, the light from the sample return (356) and reference (353) paths is coincident and interferes with high efficiency. At beamsplitter 310, a small amount of reference light (as shown by signal line 355) is sampled towards a monitor path.

In contrast to interferometers used in state of the art commercial ophthalmic OCT systems, beamsplitting towards the eye does not result in a reciprocal loss of light on the return path. Using the same input and return path through the same portion of the pupil of the eye is optimal for maintaining the easiest device alignment and field of view. The combination of the polarizing beamsplitter (e.g., the PBS 303) with the retardance of the sample arm optics (e.g., the quarter wave plate 304) acts as a polarization dependent optical isolator, or circulator. The total retardance of the sample arm acts to rotate the output polarization relative to its input state (i.e., from 'S' state to 'P' state or vice versa). A similar overall polarization rotation effect can be achieved with Faraday rotator optics. While such implementations would be within the scope of this invention, these materials are not currently widely available, with high transmission efficiency, at low cost for ophthalmically relevant wavelengths around 800 nm and 1050 nm. The sample arm optics (particularly the eye 314) introduce small but significant retardance which somewhat undermine the performance of this polarization dependent isolator. This embodiment/design can be altered slightly to compensate a median 'with the rule' population normal by altering the orientation and thickness of the waveplate such that the total retardance is as close as possible to half a wavelength oriented at 45 degrees relative to the input polarization.

Figure 4:
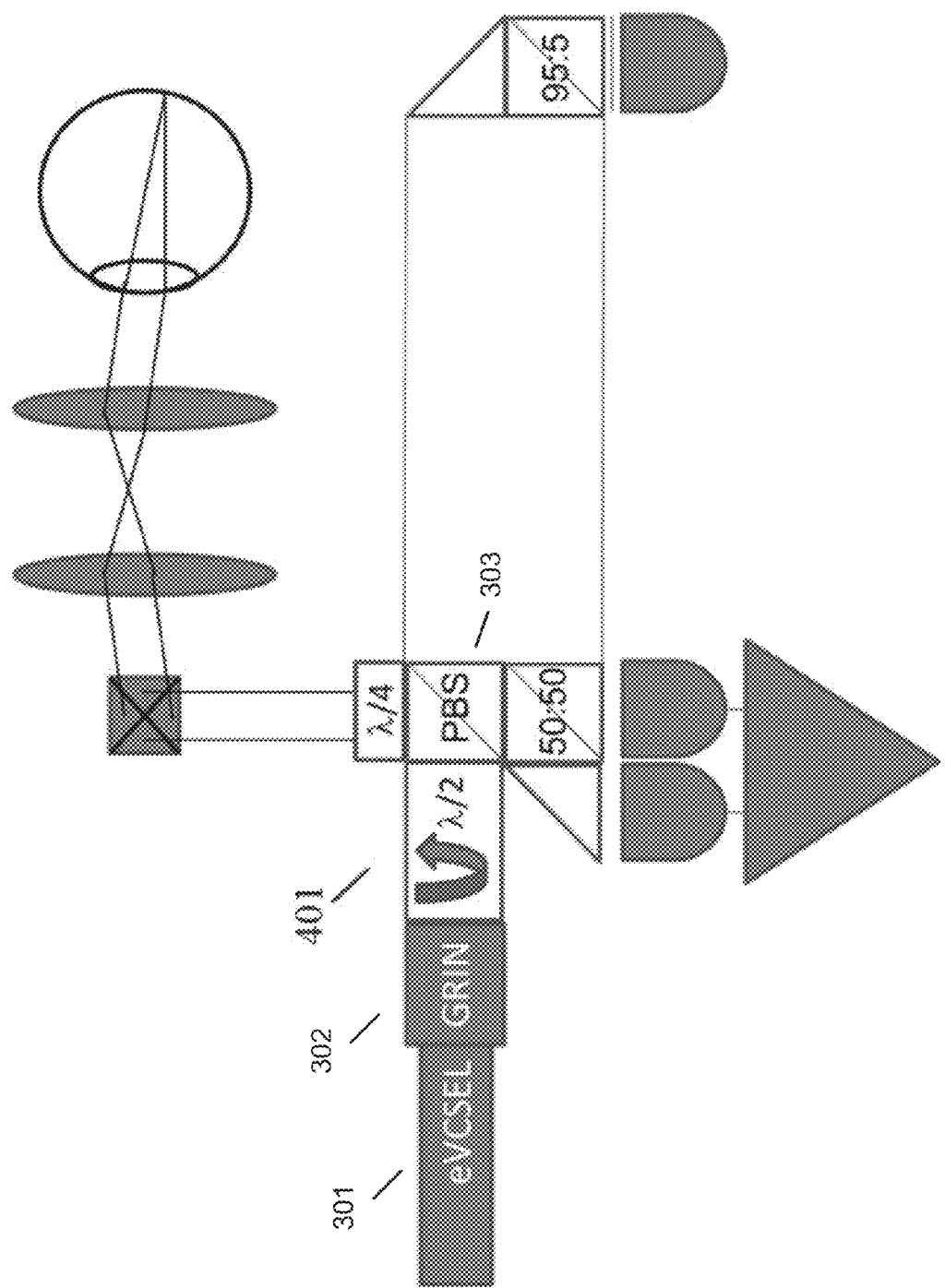
FIG. 4 is a schematic illustration of another exemplary interferometer design according to the present invention.

The design/embodiment illustrated in FIG. 4 is similar to that illustrated in FIG. 3A and/or FIG. 3B, except that a polarization manipulating element 401 (e.g., a rotatable birefringent half waveplate) between the GRIN lens 302 and the polarizing beamsplitter 303 is used to control the polarization of the source 301. The function of the polarization manipulating element 401 could similarly be performed by a faraday rotator, Dove prism, or other optic. The retardance of an individual eye may be compensated by allowing the orientation of the waveplate to rotate and/or tilt (effectively changing its thickness). Combinations of multiple waveplates or other polarization altering methods can be used to achieve the same goal.

Figure 5:
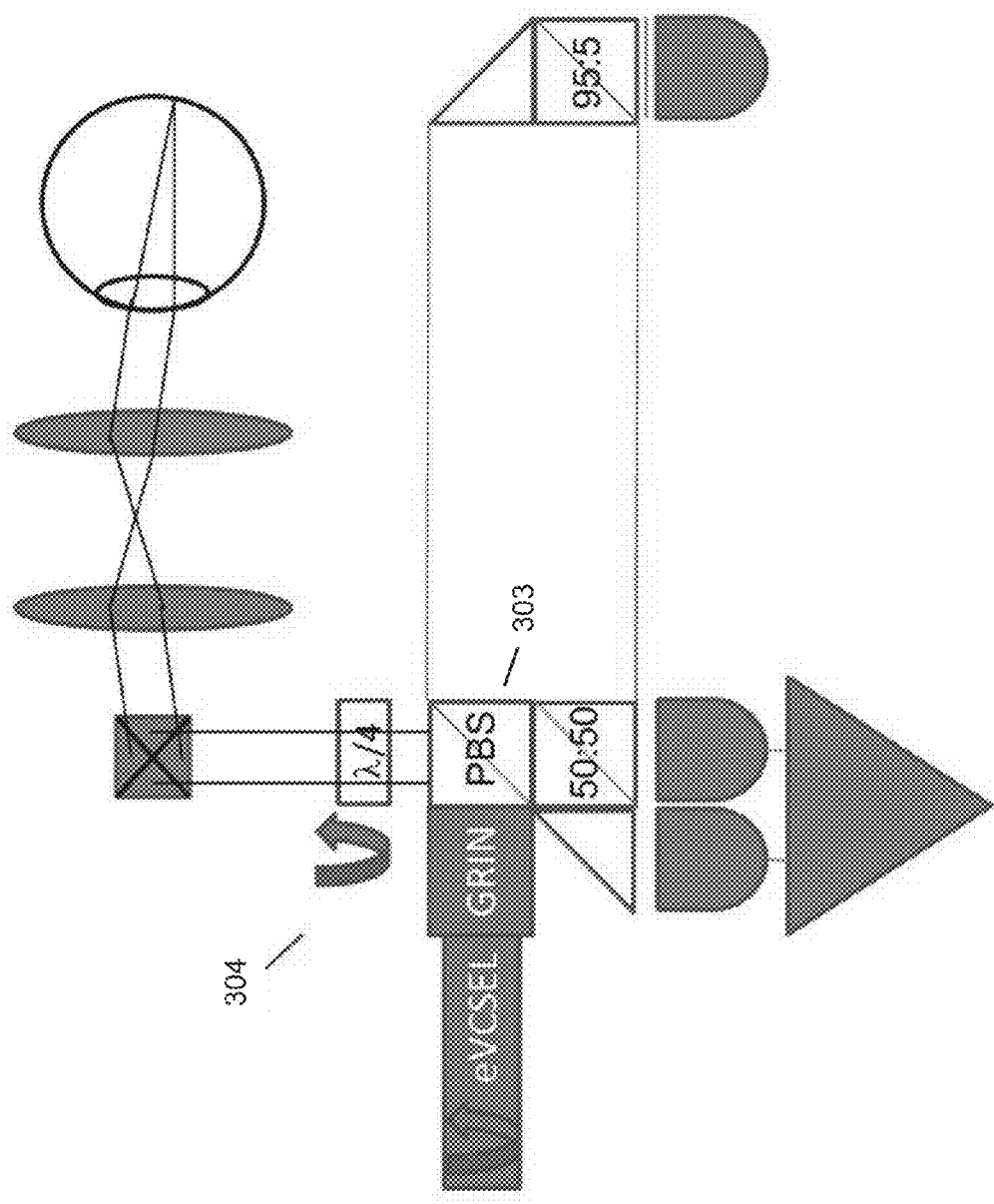
FIG. 5 is a schematic illustration of another exemplary interferometer design according to the present invention.

The embodiment illustrated in FIG. 5 is similar to that illustrated in FIG. 3A and/or FIG. 3B, except that the polarization manipulating element 304 (e.g., the quarter wave plate) is no longer cemented to the PBS 303 and is now separated from the PBS 303 allowing degrees of freedom necessary to compensate variable retardance in the sample.

Figure 6:
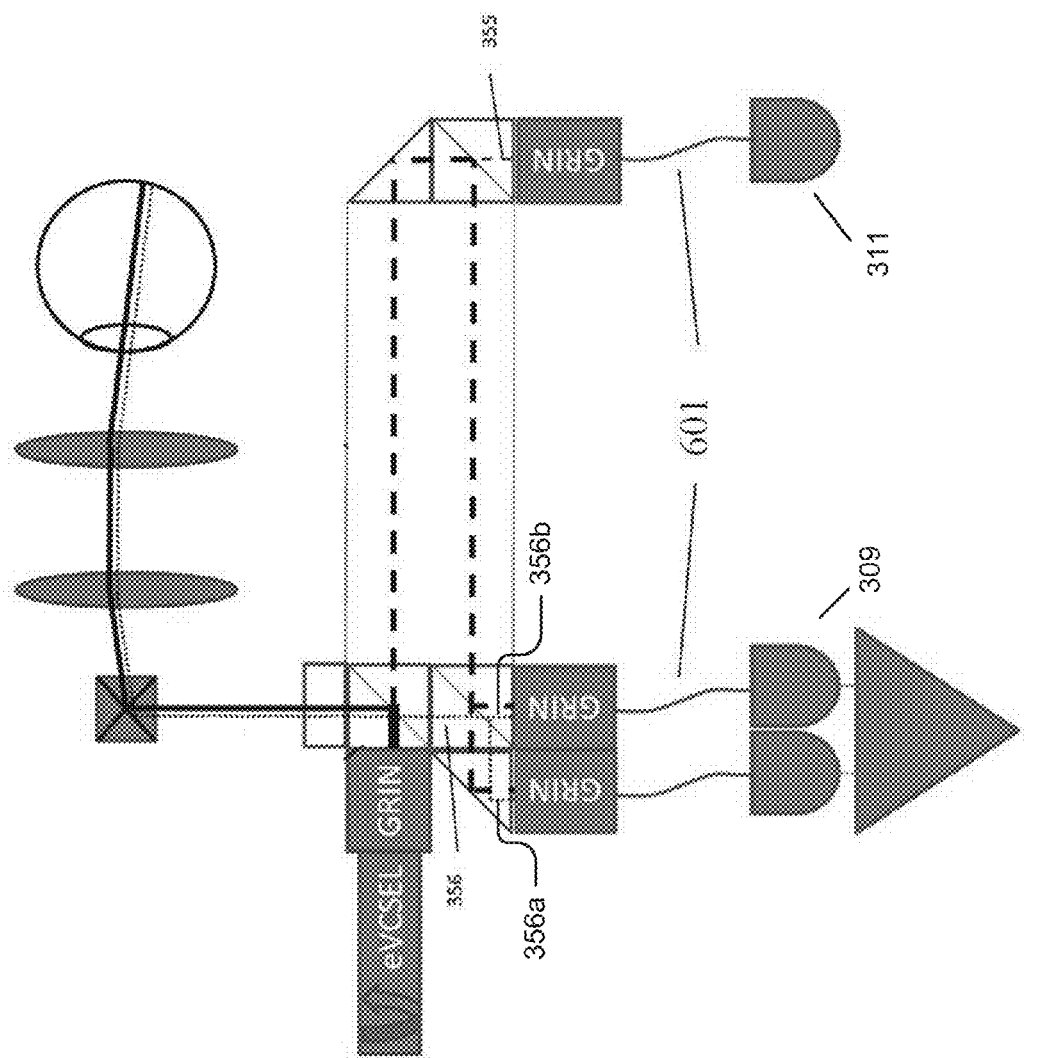
FIG. 6 is a schematic illustration of another exemplary interferometer design according to the present invention.

It is highly desirable that the path between the source and the eye does not require a coupling to single mode fiber, which is typically very lossy even for single mode sources with good beam quality because of mismatches between the single modes of the fiber and source and the low aberration and extreme precision in both position and angle required. In the detection path, the advantages of fiber may outweigh concerns about lost efficiency. The difficulty of coupling light returning from the sample path into fiber is reduced compared to launching the source into fiber. As a result of scattering of light back from the imprecise tissue of interest, the field returning towards the detection does not have a single bright mode but contains a speckle field with a range of area and incident angles somewhat larger than a single mode. Typically a single detection element is most effective when it captures only a single mode from this speckle field. A coupling to a fiber need only capture approximately the strongest portion of this speckle field to do a good job of detection. FIG. 6 illustrates an embodiment where light in the detection arm (as shown by signal line 356) of the interferometer traveling to the dual balanced detectors 309 and light from the reference arm (as shown by signal line 355) traveling to the reference light detector 311 include fiber 601. The coupling of the reference light (356*a* and 356*b*) into the fiber need not be exceedingly efficient. It may be advantageous to maintain less than perfect mode matching of the reference light and fiber to allow more alignment tolerance at the cost of lower optimal coupling efficiency.

Figure 7:
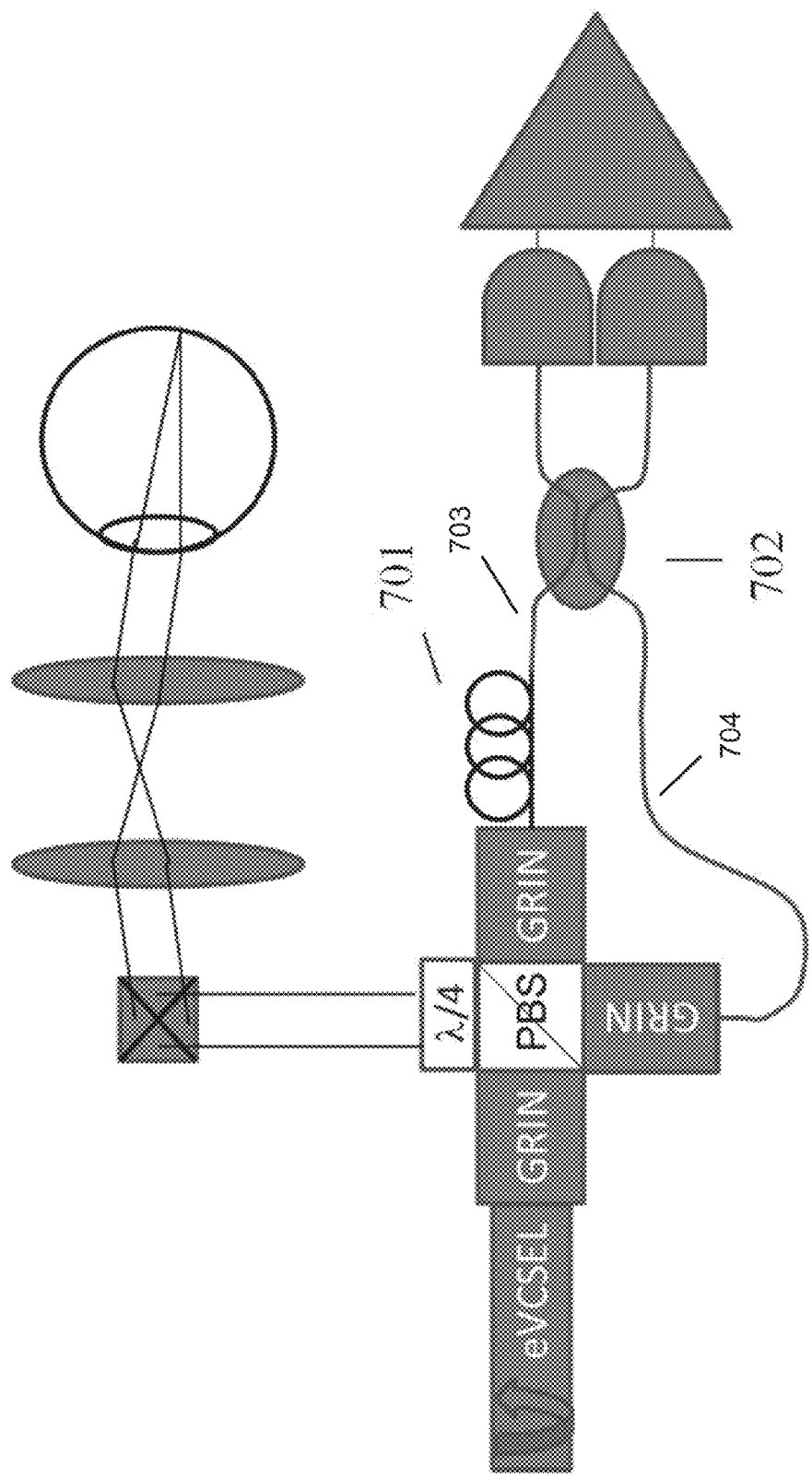
FIG. 7 is a schematic illustration of another exemplary interferometer design according to the present invention.

Similar to the embodiment discussed above with respect to FIG. 6, there are advantages of having fiber in the reference path. In particular when the sample path is long, it may be desirable that the reference path not have a similarly large physical footprint. Some inefficiency in this relatively small amount of light may be tolerable. In FIG. 7, a polarization control element 701 has been introduced in the reference path 703, although it could likewise be introduced in the fiber portion 704 after the second polarization beamsplitting. The fiber polarization controller 701 is illustrated as set of fiber loops sometimes called a 'bat ear', 'paddle', 'fiber loop', or 'LeFevre' polarization controller. This controller 701 works by introducing stress birefringence in the fiber (e.g., the fiber 703) which can be manipulated by changing the size, number and orientation of the fiber loops. Such a controller 701 could be replaced by Soleil-Babinet compensator or other inline device. In this particular embodiment, the non-polarization beamsplitter (NPBS 308) combining the reference and sample paths is replaced with a 2×2 fiber splitter 702.

Figure 8:
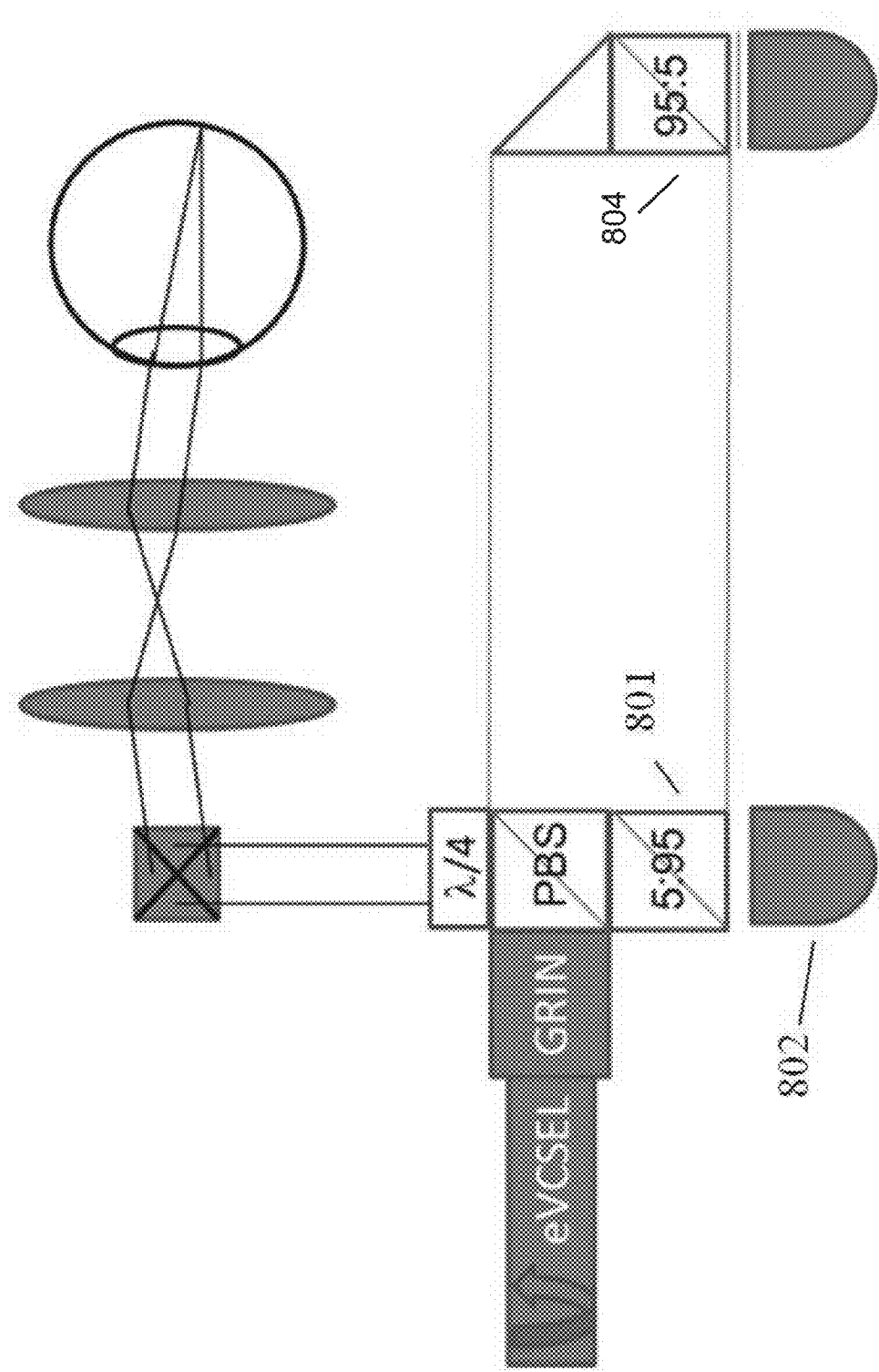
FIG. 8 is a schematic illustration of another exemplary interferometer design according to the present invention.

FIG. 8 is a schematic illustration of another interferometer design/embodiment. In some instances, the embodiment illustrated in FIG. 8 is based on a combination of the aspects discussed with respect to FIGS. 1 and 16. The embodiment is similar to that illustrated in FIG. 3A and/or FIG. 3B, except that the balanced NPBS 308 of 50:50 equal transmission ratio is now replaced with a unbalanced NPBS 801 and the dual-balanced detector 309 is replaced with a single detector 802. As depicted, the NPBS 801 has a highly unequal transmission ratio such that the majority of return sample light (e.g., 95% of the return sample light) is detected at the detector 802 for the OCT signal and the majority of reference light (e.g., 95% of reference light at beamsplitter 804) is lost.

Figure 9:
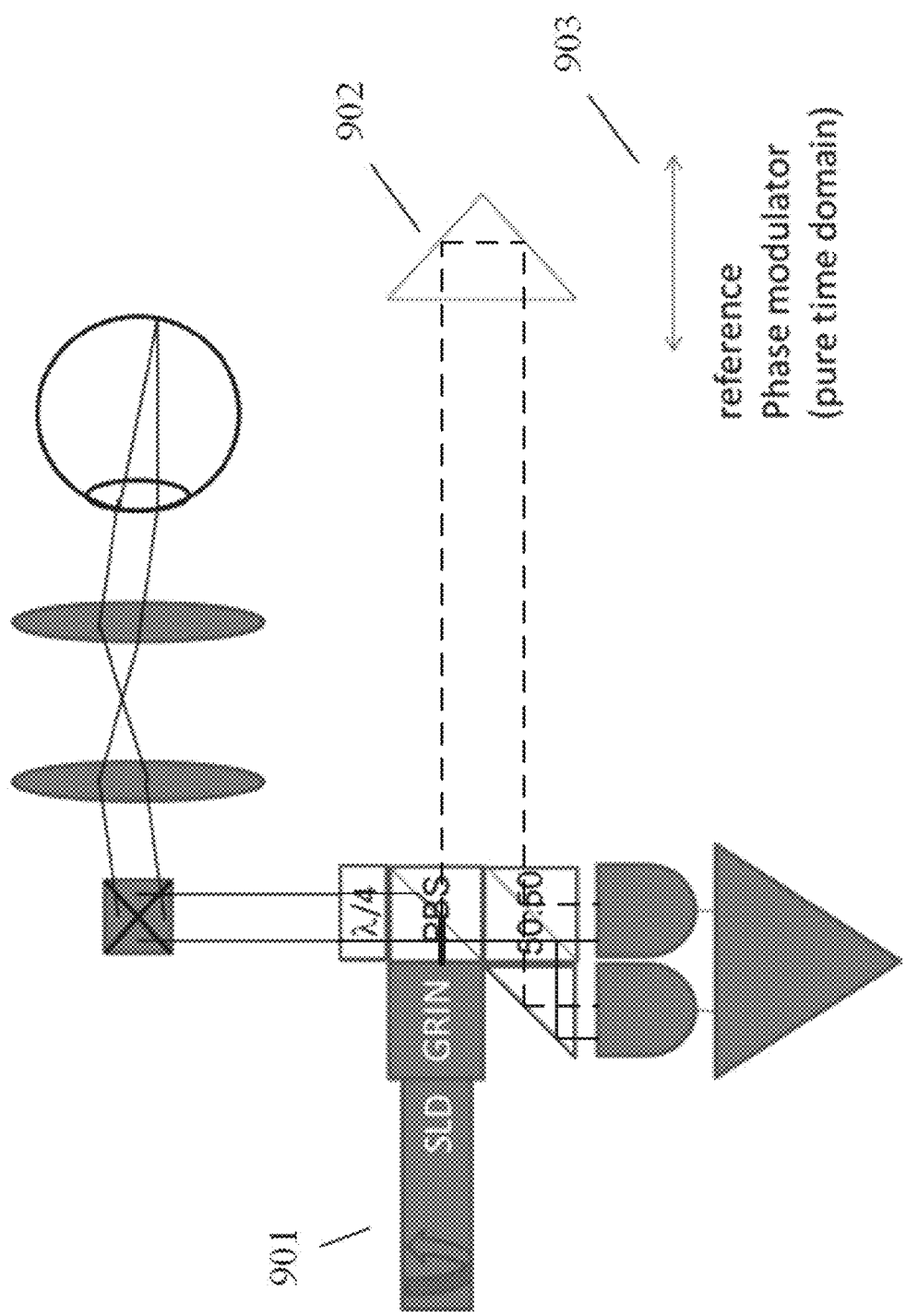
FIG. 9 is a schematic illustration of another exemplary interferometer design according to the present invention.

FIG. 9 illustrates an embodiment using an instantaneously broadband or low coherence optical radiation source, such as superluminescent diode (SLD) 901. Here the same interferometer configuration may be used for efficient time domain detection. In this case, an optical phase modulation in either the sample or reference arm is typically applied to compose an A-scan. The glass spacer block to fuse the reference arm into a monolith has been omitted in this embodiment to allow a beam reflecting prism 902, freedom to move on a stage 903 to apply the path length modulation which introduces the optical phase modulation in the reference arm.

Figure 10:
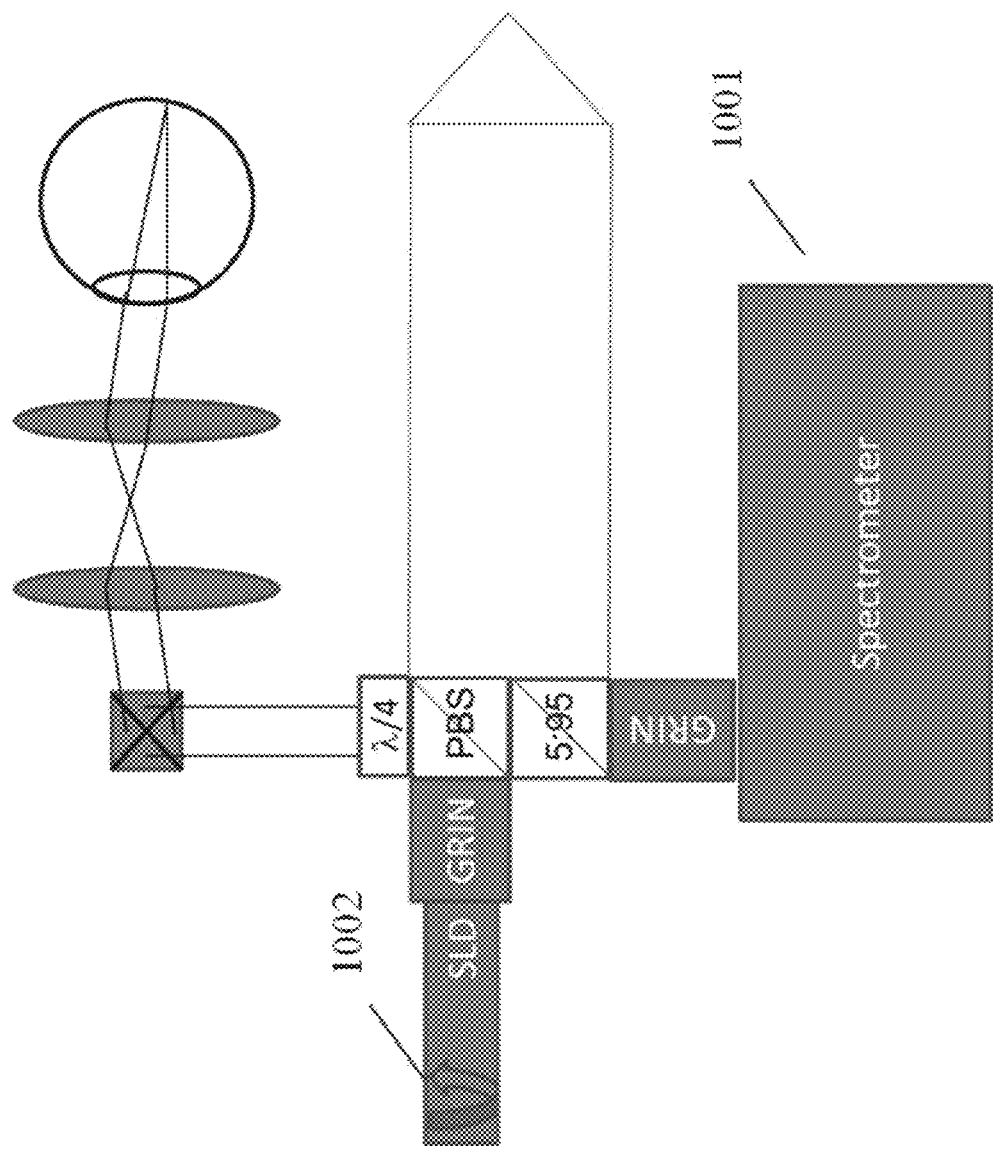
FIG. 10 is a schematic illustration of another exemplary interferometer design according to the present invention.

FIG. 10 illustrates a spectral domain OCT (SD-OCT) embodiment employing a spectrally sensitive detection, spectrometer 1001. Usually this kind of system would use a source that is instantaneously broad band or a low coherence optical radiation source, like a superluminescent diode (SLD) 1002, although there are advantages to using swept sources in combination with spectral domain detection (see for example, Yun, S. H., et al. (2004). "Pulsed-source and swept-source spectral-domain optical coherence tomography with reduced motion artifacts." *OPTICS EXPRESS* 12(23): 5614-5624). Spectral domain systems typically have low susceptibility to RIN noise (temporal variations in source power) and are frequently operated with an unbalanced detection.

Figure 11:
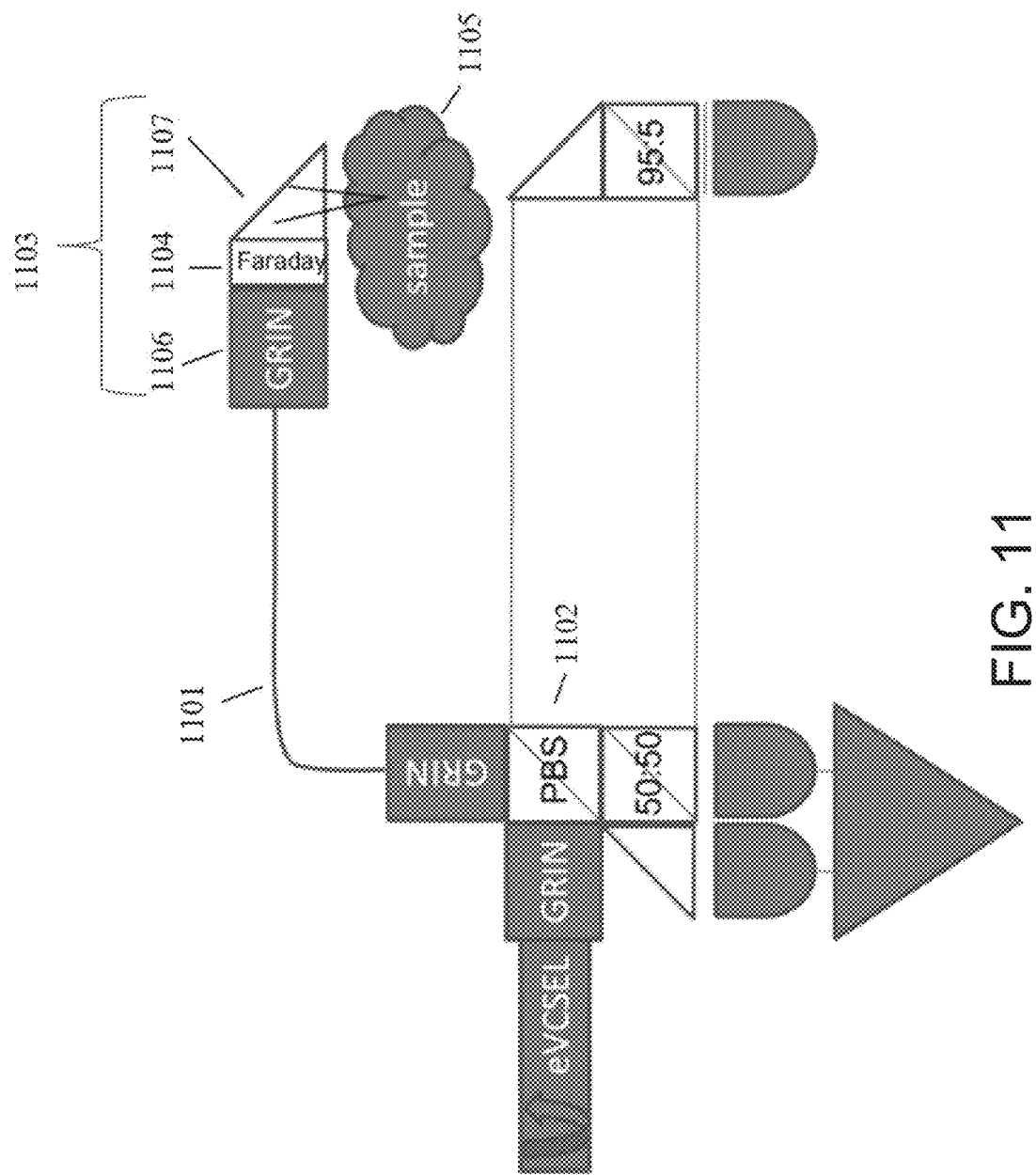
FIG. 11 is a schematic illustration of another exemplary interferometer design according to the present invention.

FIG. 11 illustrates an embodiment where the interferometer is optimized for measurement with a fiber optic catheter endoscope. A flexible portion of non-polarization maintaining fiber 1101 is used to couple light from the PBS 1102 to a rigid endoscope tip 1103. As the flexible endoscope is bent, rotated, or stressed, the birefringence of the fiber 1101 changes causing all manner of polarization changes. The polarization state within the rigid endoscope tip 1103, including focusing optics 1106 and beam directing optics 1107 is predictable. At the endoscope tip, the light passes through a faraday rotator 1104 and then hits a sample 1105. A typical epithelial tissue is very mildly birefringent at its superficial layers where there is little collagen, and may become strongly birefringent at the basement layer where collagen fibrils are dense. Light returning from the superficial layers which retains the incident polarization, upon a second pass through the faraday rotator 1104 is launched into the fiber 1101 at an orthogonal polarization to that which came from the fiber. On a second pass through the fiber 1101, the retardance of the polarization is cancelled at least for light returning from superficial layers. Again this light is in an orthogonal polarization state compared to its launch into the fiber (e.g., in 'S' polarization state) and is now transmitted as 'P' polarization state through the PBS 1102 before traveling to the detection.

Figure 12:
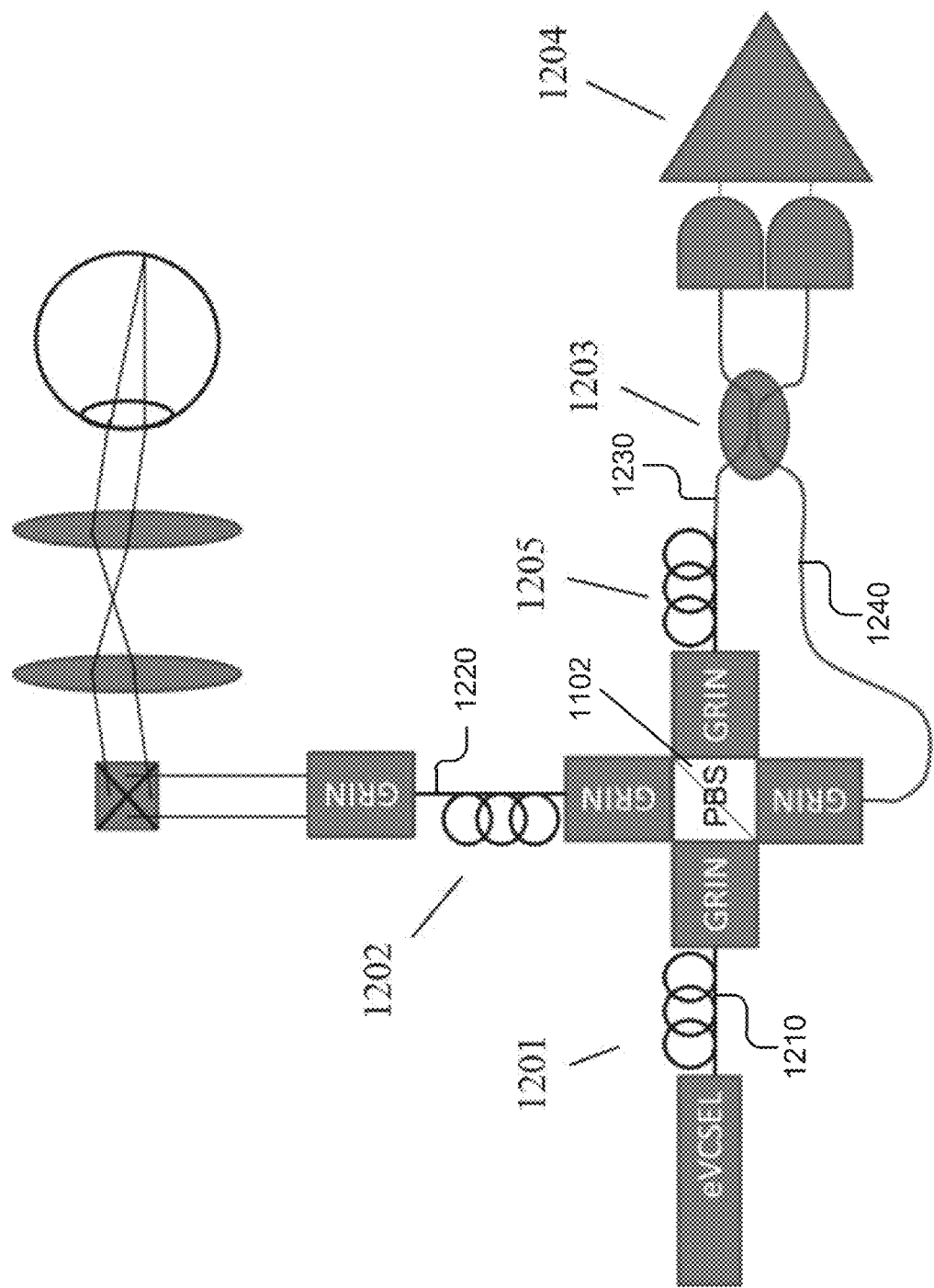
FIG. 12 is a schematic illustration of another exemplary interferometer design according to the present invention.

FIG. 12 illustrates an embodiment where fiber is used in the source, sample, reference, and/or detection paths. A fiber polarization controller 1201 is introduced in the source path 1210 to control the orientation of the source polarization relative to the component states in the sample and reference arm determined by the first beam splitting of the PBS 1102. By adjusting the input polarization, the splitting ratio between the sample and reference can be efficiently optimized. In the sample arm 1220, another fiber polarization controller 1202 introduces birefringence in addition to any birefringence introduced by the sample itself. The total retardation of the sample arm may be optimized such that the polarization state returning from the sample is orthogonal to the state input to the sample arm, and therefor is directed with high efficiency towards a non-polarizing combiner 1203 with the reference arm light implemented as a 2×2 fiber coupler, and finally terminating in a dual balanced detector 1204. Although the polarization states of the reference path after the first beamsplitting (as indicated by reference numeral 1230), and of the sample return light after the second beamsplitting (as indicated by reference numeral 1240), are parallel directly after the beamsplitting, a polarization controller 1205 is added to one of the two paths (e.g., the controller 1205 is added to the reference path 1230) to compensate polarization effects of fiber in these paths which might otherwise cause the polarizations to differ at the combining and fail to interfere with high contrast at the detection.

Figure 13:
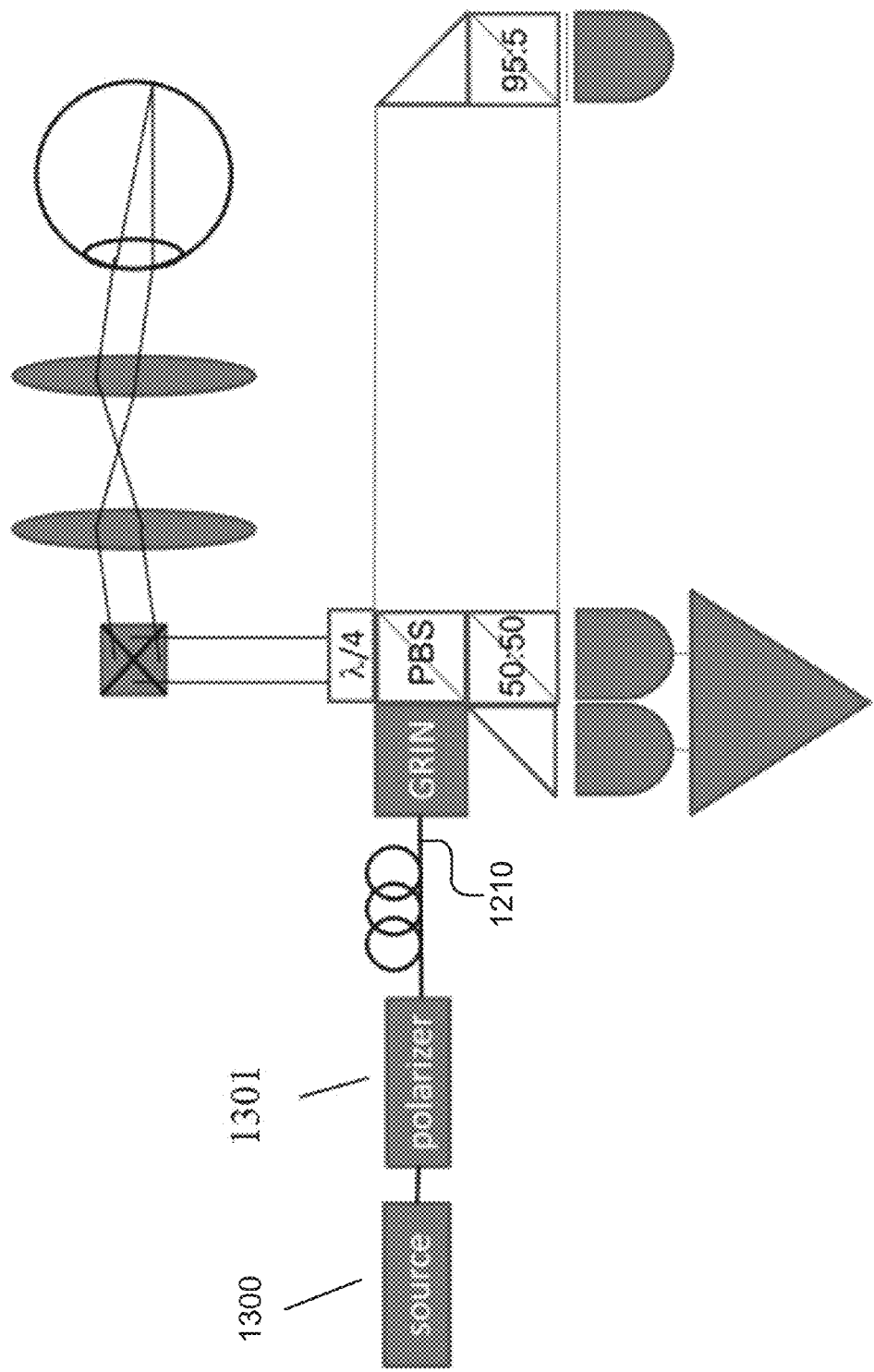
FIG. 13 is a schematic illustration of another exemplary interferometer design according to the present invention.

In the embodiment illustrated in FIG. 13, the source 1300 does not have a distinct polarization state intrinsically so an explicit polarizer 1301 is included in the source path 1210.

In the embodiment illustrated in FIG. 14, a field illumination OCT system is described incorporating the inventive aspect. In some instances, this embodiment is based on the aspect discussed in reference to FIG. 1. In field illumination, a sample 1404 is illuminated with a field of light (e.g, a line of light, a 2D region of light) instead of a single point of light. In this embodiment, the first polarization dependent beamsplitter 1401 performs beamsplitting at a surface physically distinct from the second polarization dependent beamsplitter 1402, and the non-polarizing combiner 1403 performs its combining in near contact with the second beamsplitter 1402. The first polarization dependent splitter 1401 serves to provide precise control over the splitting ratio between the sample and reference arms without requiring a wasteful attenuator in the reference. Light is directed towards the sample 1404 and returns to the second polarization splitter 1402 that is implemented as a dielectric coating on a thin glass substrate 1406. Due to the retardance by a quarter wave plate 1407 introduced in the sample path, this second splitter 1402 allows the light to take a path towards the detector 1405, rather than back along its original path towards the source 1400. On the reverse side of the same thin substrate 1406 used to support the second beamsplitter 1402, a nonpolarizing beam combiner 1403 with a high transmission is implemented. Sample return light 1408 transmitting through this NPBS 1403 and reference light 1409 reflecting off this NPBS 1403, interfere to produce a speckle pattern which is sampled by the multiple detection elements of the sensor array 1405.

The natural orientation for the sample light 1408 transmitted through the dielectric coating of the second beamsplitter 1402 is in the 'P' state. The reference light which interferes usefully will also be in the 'P' state, whereas reference light in the 'S' state will contribute only to noise. In order to achieve optimal interference, the polarization of the light launched from the reference path fiber should be in the 'P' state. As an approximation to a non-polarizing beamsplitter (NPBS) 1403 used as the combining, the second surface of the thin substrate 1406 may be any coating, or uncoated glass with a small partial reflection for 'P' polarized light. Although simple glass air reflections can be substantially polarizing, the input on both sides of this beam combiner are ideally 100% 'P' polarization and the polarizing nature of the bare glass interface does not add or remove from the ratio of sample and reference light combined.

The position of the birefringent polarization rotation in this design/embodiment is particularly advantageous for field illumination OCT. Because field illumination OCT does not have a single mode confocal restriction in the detection path, it is more susceptible to reflections from out of focus surfaces such as lenses in the sample arm optics. By placing the birefringent material between lenses in the sample path most likely to have undesirable back reflections and the interesting sample, the back reflections which do not experience a polarization rotation will be directed by the second beamsplitter 1402 back towards the source 1400 rather than towards the combiner 1403 and the detector 1405.

FIG. 15 is a schematic illustration of another exemplary interferometer design/embodiment according to the present invention. In some instances, this embodiment is based on the aspect discussed in reference to FIG. 2. Here, light is transmitted through free space optics from a low power source 1501 to a sample (e.g., eye) 1502 without passing through a single mode fiber. A fixed ratio, non polarizing dielectirc beamsplitter cube (NPBS) 1503 samples a portion of the light to use in a reference arm 1504. A polarization dependent beamsplitter (PBS) 1505 and a polarization manipulator (e.g., a birefringent retarder plate) 1508 are used to implement a non-reciprocal beamsplitting. Sample light 1510 returning from the PBS 1505 is combined with reference light 1504 at a non-polarizing beamsplitter (NPBS) or non-polarization dependent combiner 1506, illustrated as an equal ratio 2×2 fiber beamsplitter. Output from the NPBS 1506 is input to a dual balanced detector 1507.

In all embodiments described herein, the output from the detector is supplied to a processor. Data can be stored in the processor or displayed on a display. The processing and storing functions may be localized within the OCT instrument or functions may be performed on an external processing unit to which the collected data is transferred. This unit could be dedicated to data processing or perform other tasks which are quite general and not dedicated to the OCT device. A data processing system may consist of one or more processors, not necessarily located in close proximity to one another, and associated peripherals such as displays. One or more of the processors can be of the parallel processing type such as GPUs, FPGAs, or multi-core processors.

The interference between the light returning from the sample and from the reference arm causes the intensity of the interfered light to vary across the spectrum. The Fourier transform of the interference light reveals the profile of scattering intensities at different path lengths, and therefore scattering as a function of depth (z-direction) in the sample. The scattering profile as a function of depth is called an axial scan (A-scan). A set of A-scans measured at neighboring locations in the sample produces a cross-sectional image (tomogram or B-scan) of the sample. A collection of B-scans makes up a data cube or volume or volumetric image.

The foregoing description of the embodiments of the present subject matter has been presented for the purposes of illustration and description. It is not intended to be exhaustive or to limit the present embodiment of subject matter to the precise form disclosed. Many modifications and variations are possible in light of the above teaching. It is intended that the scope of the present embodiment of subject matter be limited not by this detailed description, but rather by the claims of this application. As will be understood by those familiar with the art, the present subject matter may be embodied in other specific forms without departing from the spirit or essential characteristics thereof.

The following references are hereby incorporated by reference:

PATENT DOCUMENTS

U.S. Pat. No. 7,388,672
U.S. Pat. No. 7,126,693
U.S. Pat. No. 7,145,661
U.S. Pat. No. 7,102,756
U.S. Pat. No. 6,657,727
U.S. Pat. No. 7,280,221
U.S. Pat. No. 6,501,551
U.S. Pat. No. 5,459,570

NON-PATENT LITERATURE

John, D., Burgner, C., Potsaid, B., Robertson, M., Lee, B., Choi, W. J., . . . Jayaraman, V. (2015). Wideband Electrically-Pumped 1050 nm MEMS-Tunable VCSEL for Ophthalmic Imaging. *Journal of Lightwave Technology*, 1-1. doi: 10.1109/P.2015.2397860

Yun, S. H., et al. (2004). "Pulsed-source and swept-source spectral-domain optical coherence tomography with reduced motion artifacts." *OPTICS EXPRESS* 12(23): 5614-5624

What is claimed is:

1. An interferometer for use in an optical coherence tomography (OCT) imaging system, said system having a source arm with an optical radiation source, a sample arm, a reference arm, and a detector, said interferometer comprising:
   a first polarization dependent splitting element having an input port connected to the optical radiation source, a first output port connected to the sample arm leading to a sample, said first output port transmitting light in a first polarization state towards the sample, and a second output port connected to the reference arm, said second output port transmitting light in a second polarization state different from the first polarization state;
   a second polarization dependent splitting element having an input port connected to the sample arm and an output port; and
   a substantially non-polarization dependent combiner having a first input port for receiving light that has passed through the sample arm from the output port of the second polarization dependent splitting element, a second input port for receiving light from the reference arm, and an output port for transmitting light received from the sample arm and the reference arm to the detector.

2. The interferometer as recited in claim 1, in which the first polarization dependent splitting element and the second polarization splitting element are the same.

3. The interferometer as recited in claim 1, wherein the detector is a dual-balanced detector.

4. The interferometer as recited in claim 1, wherein said optical radiation source is polarized.

5. The interferometer as recited in claim 1, further comprising a polarizer between the optical radiation source and the first polarization dependent beamplitting element.

6. The interferometer as recited in claim 1, wherein power in the reference arm is adjusted by adjusting the polarization state of the source relative to the polarization dependence of the first polarization dependent splitting element.

7. The interferometer as recited in claim 1, wherein light transmitted through the second polarization dependent beamsplitting element has a polarization state orthogonal to the first polarization state of the light transmitted to the sample arm through the first polarization dependent splitting element.

8. The interferometer as recited in claim 1, further comprising a polarization manipulating element for manipulating a polarization state of the light transmitted through it, said polarization manipulating element placed between the first or the second polarization dependent splitting element and the sample.

9. The interferometer as recited in claim 1, further comprising a polarization manipulating element for manipulating a polarization state of the light transmitted through it, said polarization manipulating element placed between the optical radiation source and the first polarization dependent splitting element.

10. The interferometer as recited in claim 1, wherein the light from the optical radiation source to the sample is transmitted without coupling to a single mode optical fiber.

11. The interferometer as recited in claim 1, wherein the first and the second polarization dependent elements are combined into a single polarization dependent beamsplitting element having four ports, wherein a first port receives light from the optical radiation source, a second port transmits light in the first polarization state towards the sample, a third port transmits light in the second polarization state to the reference arm, and a fourth port transmits light returned from the sample to the non-polarization dependent combiner.

12. The interferometer as recited in claim 1, wherein the optical radiation source is a low coherence optical radiation source and the detector is a spectrally sensitive detector, said spectrally sensitive detector being a spectrometer.

13. The interferometer as recited in claim 1, wherein said light source is a swept source.

14. The interferometer as recited in claim 1, further comprising a polarization manipulating element in the reference arm.

15. An interferometer for use in an optical coherence tomography (OCT) imaging system, said system having a swept light source, a sample arm leading to a sample to be imaged, a reference arm, and a dual balanced detector, said interferometer comprising:

free space optics for directing light from the swept light source to the sample, said free space optics comprising non-reciprocal beamsplitting elements including a polarization dependent beamsplitting element and a polarization manipulator, said polarization dependent beamsplitting element having an input port for receiving light from the swept light source, a first output port for sending light towards the sample, and a second output port for transmitting light returning from the sample, said polarization manipulator configured to manipulate the polarization state of the light transmitted through the manipulator and is located in between the polarization dependent beamsplitting element and the sample; and a non-polarization dependent combiner having a first input port for receiving light returning from the sample from the polarization dependent beamsplitting element, a second input port for receiving light from the reference arm, and an output port for transmitting light received from the sample and the reference arm to the dual balanced detector.

16. The interferometer as recited in claim 15, wherein the free space optics further comprise a non-polarizing dielectric beamsplitting element for splitting light from the swept light source into the sample arm and the reference arm, wherein an output port of the non-polarizing dielectric beamsplitting element is connected to the input port of the polarization dependent beamsplitting element.

17. The interferometer as recited in claim 15, wherein the polarization manipulator is a quarter wave plate.

18. The interferometer as recited in claim 15, wherein said swept light source has an output power of less than 5 mW.

19. The interferometer as recited in claim 15, wherein the sample is an eye.

20. An interferometer for use in an optical coherence tomography (OCT) imaging system, said system having an optical radiation source, a sample arm, a reference arm, and a detector, said interferometer comprising:

a polarization dependent splitting element having a first port for receiving light from the optical radiation source, a second port for transmitting light in a first polarization state to the sample arm, a third port for transmitting light in a second polarization state different from the first polarization state to the reference arm, and a fourth port for transmitting light returned from the sample arm; and a substantially non-polarization dependent combiner having a first input port for receiving light that has passed through the sample arm and exited through the fourth port of the polarization dependent splitting element, said non-polarization dependent combiner having a second input port for receiving light from the reference arm, said non-polarization dependent combiner having an output port for transmitting light received from the sample arm and the reference arm to the detector.

* * * * *

UNITED STATES PATENT AND TRADEMARK OFFICE
CERTIFICATE OF CORRECTION

PATENT NO. : 9,778,020 B2
APPLICATION NO. : 15/159601
DATED : October 3, 2017
INVENTOR(S) : Alexandre R. Tumlinson et al.

It is certified that error appears in the above-identified patent and that said Letters Patent is hereby corrected as shown below:

In Column 3, Line 10, delete "beamplitting" and insert -- beamsplitting --, therefor.

In Column 13, Line 24, delete "dielectirc" and insert -- dielectric --, therefor.

In Column 14, Line 23, delete "10.1109/P.2015." and insert -- 10.1109/jlt.2015. --, therefor.

In Column 14, Line 63, in Claim 5, delete "beamplitting" and insert -- beamsplitting --, therefor.

In Column 15, Line 48, in Claim 15, delete "beamplitting" and insert -- beamsplitting --, therefor.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*